(12) United States Patent
Fujita et al.

(10) Patent No.: US 9,993,370 B2
(45) Date of Patent: Jun. 12, 2018

(54) ULTRASONIC WELDING DEVICE

(71) Applicant: ZUIKO CORPORATION, Settsu-shi, Osaka (JP)

(72) Inventors: Yukihiko Fujita, Osaka (JP); Hideyuki Nakamura, Osaka (JP)

(73) Assignee: ZUIKO CORPORATION (JP)

( * ) Notice: Subject to any disclaimer, the term of this patent is extended or adjusted under 35 U.S.C. 154(b) by 150 days.

(21) Appl. No.: 15/107,270

(22) PCT Filed: Dec. 10, 2014

(86) PCT No.: PCT/JP2014/082745
§ 371 (c)(1),
(2) Date: Jun. 22, 2016

(87) PCT Pub. No.: WO2015/098534
PCT Pub. Date: Jul. 2, 2015

(65) Prior Publication Data
US 2017/0027763 A1    Feb. 2, 2017

(30) Foreign Application Priority Data
Dec. 26, 2013    (JP) .................. 2013-269409

(51) Int. Cl.
| | | |
|---|---|---|
| B32B 37/00 | (2006.01) | |
| A61F 13/15 | (2006.01) | |
| A61F 13/496 | (2006.01) | |
| B29C 65/08 | (2006.01) | |
| B29C 65/78 | (2006.01) | |
| B29C 65/00 | (2006.01) | |
| B29L 31/48 | (2006.01) | |

(52) U.S. Cl.
CPC ...... *A61F 13/15739* (2013.01); *A61F 13/496* (2013.01); *B29C 65/086* (2013.01);
(Continued)

(58) Field of Classification Search
CPC ..... B29C 65/08; B29C 65/086; B29C 65/087; B29C 65/7885; B29C 65/7894;
(Continued)

(56) References Cited

U.S. PATENT DOCUMENTS
| | | | |
|---|---|---|---|
| 3,996,093 A | 12/1976 | Winnemoller | |
| 4,380,446 A | 4/1983 | Dickson et al. | |

(Continued)

FOREIGN PATENT DOCUMENTS
| | | |
|---|---|---|
| CN | 1179128 A | 4/1998 |
| CN | 102209513 A | 10/2011 |

(Continued)

OTHER PUBLICATIONS

European Search Reported dated Dec. 14, 2016.
Japanese Office Action dated Jul. 25, 2017.
Chinese Office Action dated Mar. 15, 2017.

*Primary Examiner* — James Sells
(74) *Attorney, Agent, or Firm* — Gerald E. Hespos; Michael J. Porco; Matthew T. Hespos

(57) ABSTRACT

The ultrasonic welding device includes a rotary support mechanical assembly rotatable about a rotation axis and operable to support a sheet over a circumference centered on the rotation axis, the sheet being continuously supplied; and a horn and an anvil operable to sandwich the sheet supported over the rotary support mechanical assembly to thereby weld the sheet. The rotary support mechanical assembly includes a rotary member rotatable about the rotation axis, a plurality of sheet support members each having a support surface for supporting the sheet, and a mounting section for allowing the plurality of sheet support members to be attached to the rotary member in a state that the sheet support members lie on the same circumference about the rotation axis, and allowing attaching positions of the sheet support members to the rotary member to be adjusted in radial directions centered on the rotation axis.

5 Claims, 15 Drawing Sheets

(52) U.S. Cl.
CPC ........ *B29C 65/087* (2013.01); *B29C 65/7885* (2013.01); *B29C 65/7894* (2013.01); *B29C 66/0326* (2013.01); *B29C 66/1122* (2013.01); *B29C 66/431* (2013.01); *B29C 66/8167* (2013.01); *B29C 66/81465* (2013.01); *B29C 66/8362* (2013.01); *B29C 66/83511* (2013.01); *B29C 66/8412* (2013.01); *A61F 2013/15869* (2013.01); *B29C 66/82263* (2013.01); *B29C 66/92613* (2013.01); *B29L 2031/4878* (2013.01)

(58) Field of Classification Search
CPC .............. B29C 66/1122; B29C 66/431; B29C 66/81465; B29C 66/83511; A61F 13/15739; A61F 13/496
USPC ........................................................ 156/73.1
See application file for complete search history.

(56) References Cited

U.S. PATENT DOCUMENTS

| | | |
|---|---|---|
| 5,643,396 A | 7/1997 | Rajala |
| 5,660,679 A | 8/1997 | Rajala |
| 5,667,608 A | 9/1997 | Rajala et al. |
| 6,537,403 B1 | 3/2003 | Blenke et al. |
| 9,333,705 B1 * | 5/2016 | Fujita ................ B29C 66/72343 |
| 9,358,159 B2 * | 6/2016 | Fujita ................ B29C 66/72343 |
| 9,452,565 B2 * | 9/2016 | Fujita .................. B29C 66/8412 |
| 2002/0148548 A1 | 10/2002 | Murie |
| 2010/0116409 A1 | 5/2010 | Yamamoto |
| 2013/0174965 A1 | 7/2013 | Yamamoto |
| 2015/0202727 A1 | 7/2015 | Yamamoto et al. |
| 2016/0107377 A1 | 4/2016 | Fujita et al. |

FOREIGN PATENT DOCUMENTS

| | | |
|---|---|---|
| EP | 2990181 A1 | 2/2016 |
| EP | 2990181 A1 | 3/2016 |
| GB | 1409077 A | 10/1975 |
| JP | 48-068666 | 9/1973 |
| JP | 57-86408 | 5/1982 |
| JP | 10-513128 | 12/1998 |
| JP | 2004330622 A | 11/2004 |
| JP | 2005205026 A | 8/2005 |
| JP | 2007030236 A | 2/2007 |
| JP | 3988835 | 7/2007 |
| JP | 2013-193450 | 9/2013 |
| WO | 9623645 A1 | 8/1996 |
| WO | 2012042842 A1 | 4/2012 |

* cited by examiner

FIG. 12
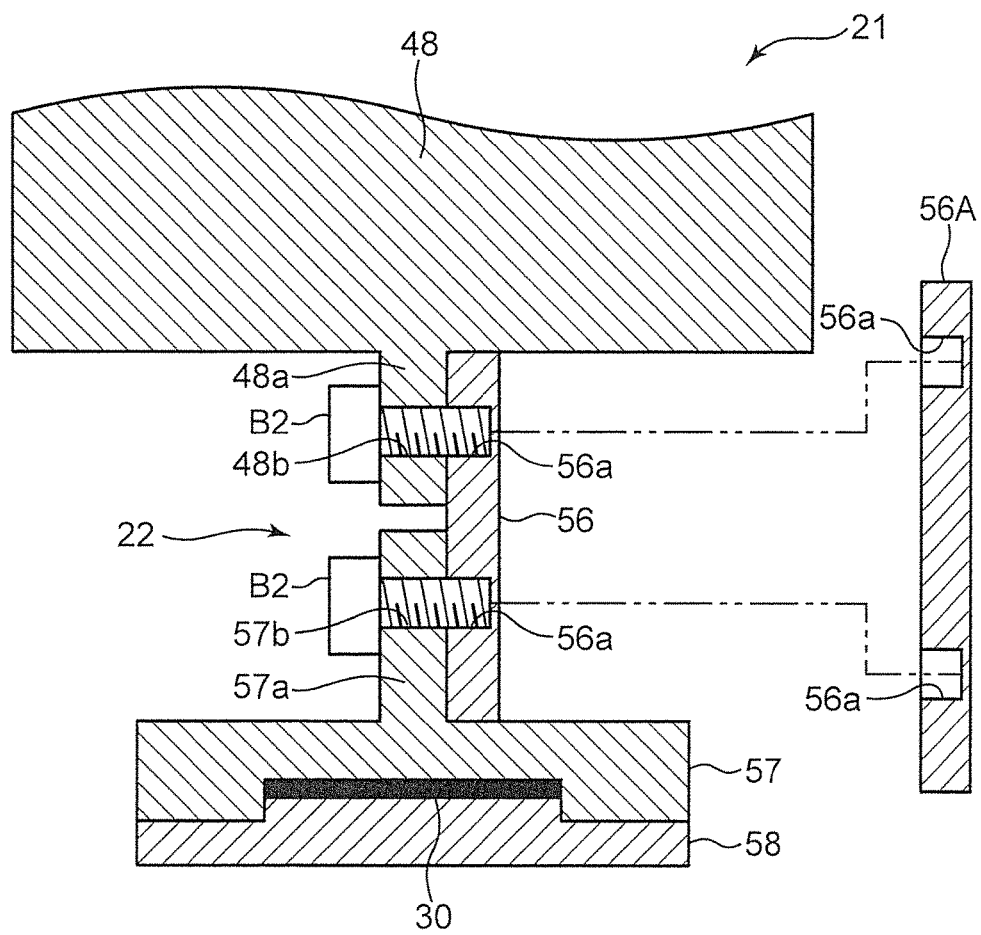
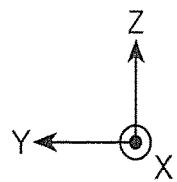

ULTRASONIC WELDING DEVICE

TECHNICAL FIELD

The present invention relates to an ultrasonic welding device for ultrasonically welding an object to be welded.

BACKGROUND ART

Conventionally, there are known ultrasonic welding devices (for example, Japanese Patent Publication No. 3988835) for ultrasonically welding an object to be welded (web) to form disposable diapers, for example.

An ultrasonic welding device disclosed in Japanese Patent Publication No. 3988835 includes a drum having an outer surface configured to support an object to be welded that is continuously supplied, the drum being rotatable about a predetermined rotation axis, and a horn and an anvil attached to the drum to thereby revolve about the rotation axis and sandwich the object supported over the outer surface of the drum to ultrasonically weld the object.

When one of the horn and the anvil is defined as a first welding tool and the other of the horn and the anvil is defined as a second welding tool, the first welding tool is attached to the drum in such a manner as to be movable relative to the second welding tool so that the first welding tool can move across the object supported over the outer surface of the drum.

According to the ultrasonic welding device disclosed in Japanese Patent Publication No. 3988835, the drum rotates integrally with the horn and the anvil. Therefore, the rotation of the drum allows the object to be welded between the horn and the anvil while being conveyed.

Thus, the period of conveying the object can also be used as a period of welding, unlike the case where an object to be welded is fed into the space between a horn and an anvil secured at a position. Therefore, it is possible to obtain a sufficient welding strength while conveying the object at a high speed.

By the way, it is necessary to change the space between adjacent welding positions of the object, according to the design of a product such as size that is made of the welded object.

Here, in order to increase the space between adjacent welding positions, it is necessary to increase the circumference of the drum so that the circumference over which the object is welded by the welding tools is increased. On the other hand, in order to reduce the space between adjacent welding positions, it is necessary to reduce the circumference of the drum.

However, in the ultrasonic welding device disclosed in Japanese Patent Publication No. 3988835, the drum is used to support the object to be welded. Therefore, it is necessary to replace the drum to change the circumference of the drum.

Here, the drum is mounted with the anvil, the horn, and a structure for connecting these components to the drum. Therefore, there is a problem that the work of replacing the drum is very troublesome.

SUMMARY OF INVENTION

The present invention aims to provide an ultrasonic welding device allowing easy adjustment for changing the space between adjacent welding positions.

In order to solve the above-mentioned problem, the present invention provides an ultrasonic welding device for ultrasonically welding an object to be welded, comprising: a rotary support mechanical assembly rotatable about a predetermined rotation axis and operable to support the object over a circumference centered on the rotation axis, the object being continuously supplied; and at least a pair of a horn and an anvil attached to the rotary support mechanical assembly to thereby revolve about the rotation axis and sandwich the object supported over the rotary support mechanical assembly to weld the object, when one of the horn and the anvil is defined as a first welding tool and the other of the horn and the anvil is defined as a second welding tool, the first welding tool being attached to the rotary support mechanical assembly in such a manner as to be movable relative to the second welding tool between a position to sandwich the object in cooperation with the second welding tool and a position away from the second welding tool, wherein the rotary support mechanical assembly includes a rotary member rotatable about the rotation axis, a plurality of object support members each having a support surface for supporting the object, and an attaching mechanism for allowing the plurality of object support members to be attached to the rotary member in a state that the object support members lie on the same circumference about the rotation axis, and allowing attaching positions of the object support members to the rotary member to be adjusted in radial directions centered on the rotation axis.

According to the present invention, it is possible to allow easy adjustment for changing the space between adjacent welding positions.

BRIEF DESCRIPTION OF DRAWINGS

FIG. 12 is a sectional view taken along the line XII-XII in FIG. 9.

DESCRIPTION OF EMBODIMENTS

Hereinafter, an embodiment of the present invention will be described with reference to the accompanying drawings.

It should be noted that the following embodiment illustrates an example of the invention, which therefore does not limit the protection scope of the invention.

Figure 1:
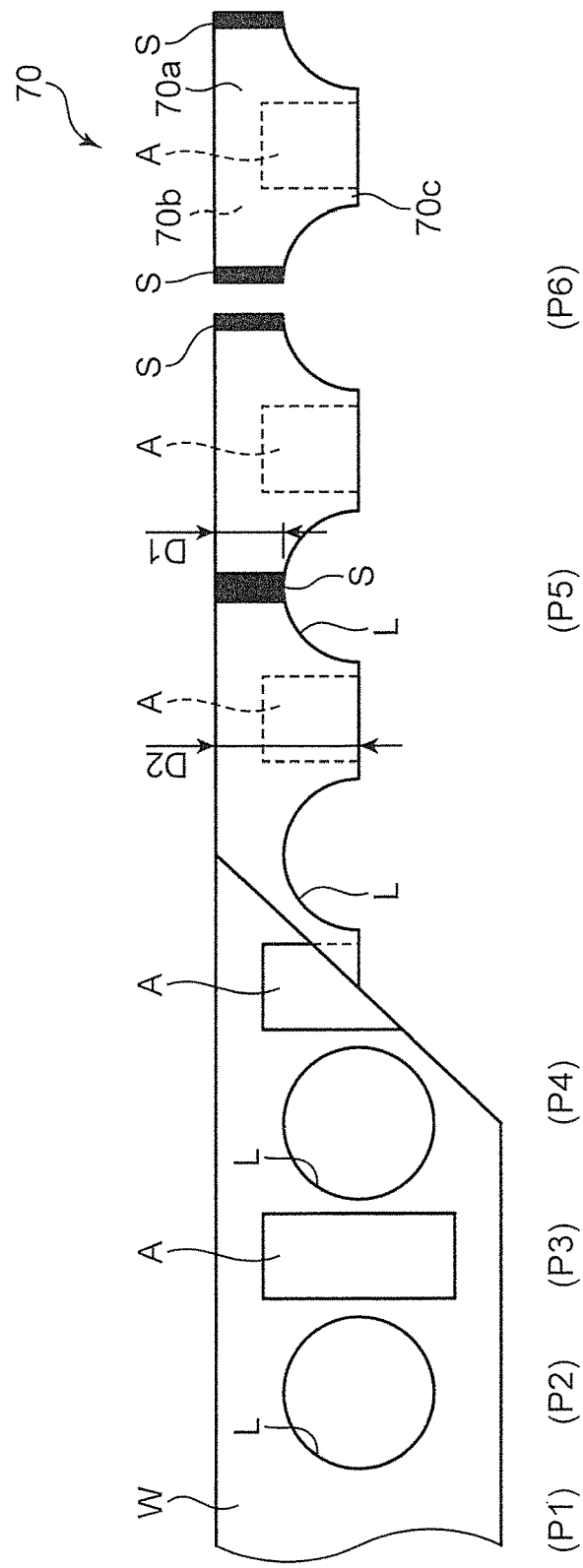
FIG. 1 is a process diagram for explaining a method of producing disposable diapers with an ultrasonic welding device according to the present invention.

With reference to FIG. 1, a disposable diaper 70 includes, when it is worn, a front abdominal section 20a disposed on the abdomen of a wearer, a rear dorsal section 70b disposed on the buttocks of the wearer, and a crotch section 70c which extends from the front abdominal section 70a, passing between the legs of the wearer, up to the rear dorsal section 70b.

Opposite lateral edge portions of the front abdominal section 70a are welded to opposite lateral edge portions of the rear dorsal section 70b via two weld sections S in such a manner that the front abdominal section 70a and the rear dorsal section 70b are connected in a ring.

In the following, a method of producing disposable diapers 70 will be described.

<Conveyance Step P1>

In a conveyance step P1, a sheet W extending in a specific direction is conveyed in its longitudinal direction. In the description hereafter, the flow direction of the sheet W will be referred to as transverse direction, and the direction perpendicularly intersecting the transverse direction in FIG. 1 will be referred to as vertical direction.

The sheet W includes an inner sheet which faces the body surface of the wearer when it is worn, an outer sheet which faces away from the wearer when it is worn, and an elastic member sandwiched between the inner sheet and the outer sheet.

<Leg Hole Formation Step P2>

In a leg hole formation step P2, leg holes L are formed in a central portion of the sheet W in the vertical direction.

A portion between each two leg holes L in the sheet W corresponds to the crotch section 70c. Further, in the sheet W, both sides of each portion corresponding to the crotch section 70c in the vertical direction respectively correspond to the front abdominal section 70a and the rear dorsal section 70b.

<Absorber Bonding Step P3>

In an absorber bonding step P3, absorbers A are bonded to the sheet W each at a position between two leg holes L.

The absorber A includes a permeable sheet having liquid permeability, a water-repellent sheet having water-repellency and breathability, and an absorbent core sandwiched between the permeable sheet and the water-repellent sheet.

A method has been described in which the absorbers A are bonded onto the sheet W. Alternatively, absorbent cores may be sandwiched and bonded between the inner sheet and the outer sheet of the sheet W. In this case, the inner sheet includes a sheet having liquid permeability, and the outer sheet includes a sheet having water-repellency and breathability.

<Fold-in-Half Step P4>

In a fold-in-half step P4, the sheet W having the absorbers A placed thereon is folded in half in the vertical direction. As a result, portions corresponding to the front abdominal section 70a and portions corresponding to the rear dorsal section 70b in the sheet W are placed on each other.

<Welding Step P5>

In a welding step P5, between adjacent absorbers A in the sheet W folded in half (object to be welded), a portion corresponding to a lateral edge portion of the front abdominal section 70a and a portion corresponding to a lateral edge portion of the rear dorsal section 70b are ultrasonically welded.

Specifically, in the welding step P5, the sheet W is ultrasonically welded over a range including a position at which cutting is performed in a cutting step P6 described below.

Weld sections S are each formed over a welding range D1 extending in the vertical direction of the portion corresponding to the lateral edge portion of the front abdominal section 70a and the portion corresponding to the lateral edge portion of the rear dorsal section 70b.

<Cutting Step P6>

In the cutting step P6, the sheet W is cut along a cutting line extending in the vertical direction at a central position of each weld section S formed in the welding step P5. As a result, the sheet W (continuous member) is cut into each disposable diaper 70.

In the following, an ultrasonic welding device 1 that performs the welding step P5 will be described with reference to FIG. 2.

The ultrasonic welding device 1 is used for ultrasonically welding a sheet W that has folded in the fold-in-half step P4 and introduced via a feed-in roller F1, and feeding the welded sheet W to the cutting step P6 via a feed-out roller F2.

Figure 2:
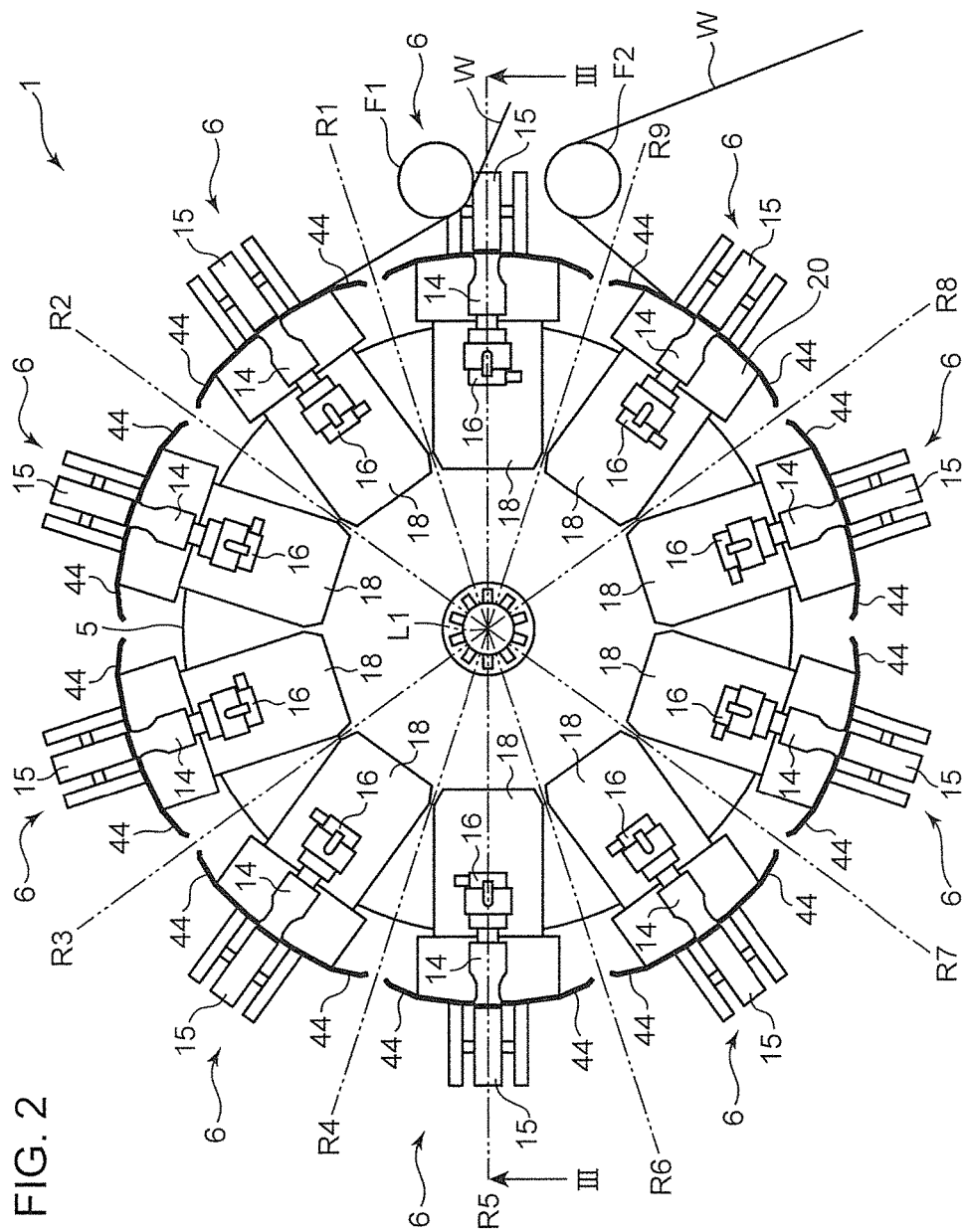
FIG. 2 is a front view of an essential part of the ultrasonic welding device according to the present invention.
Figure 3:
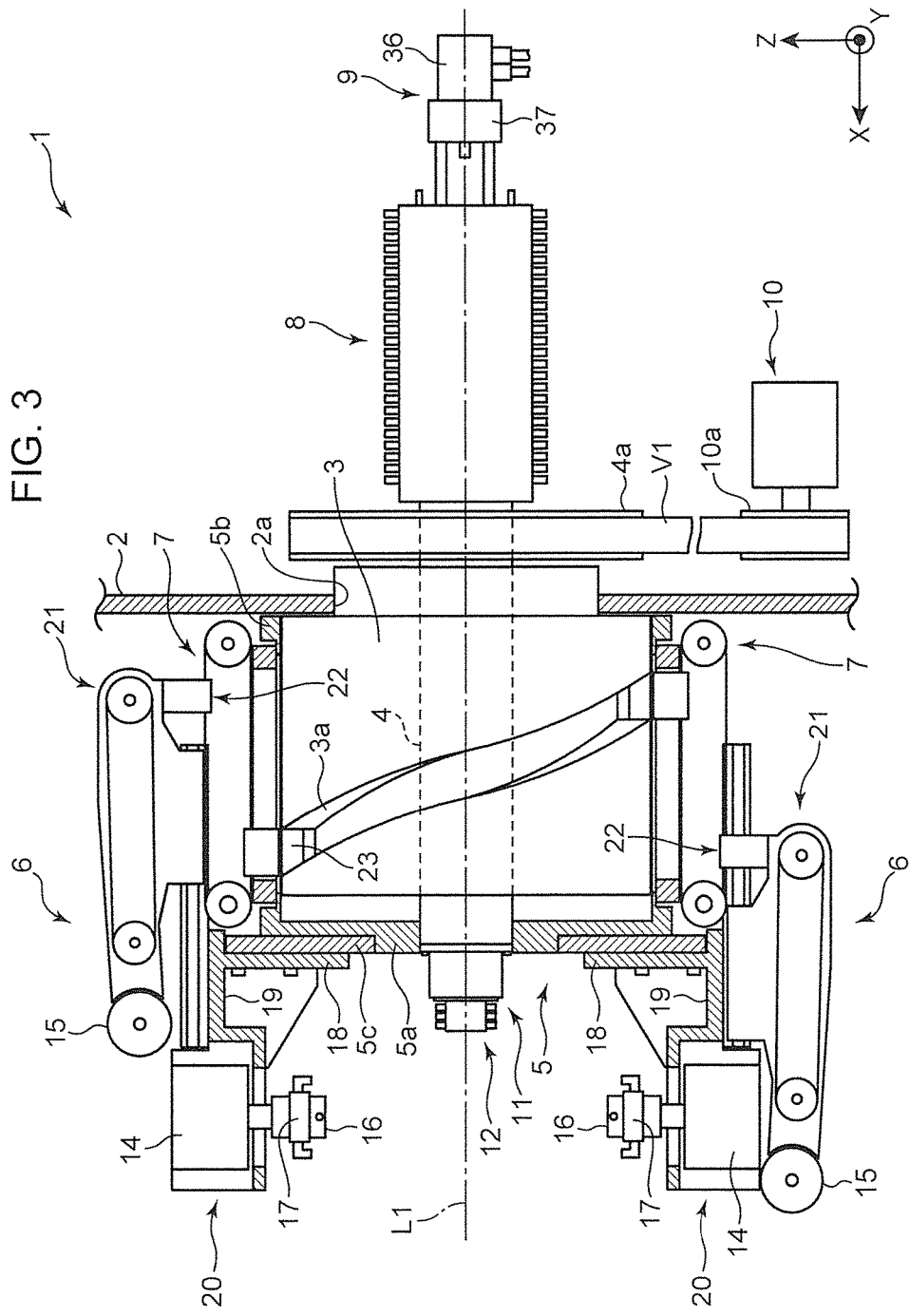
FIG. 3 is a sectional view taken along the line III in FIG. 2.

Specifically, the ultrasonic welding device 1 includes, as shown in FIGS. 2 and 3, a drive shaft support member 2 standing on a predetermined work surface, a cam drum (driving mechanism) 3 secured to the drive shaft support member 2, cam followers (driving mechanism) 23 disposed in a cam groove 3a of the cam drum 3, a drive shaft 4 supported in a manner rotatable about a rotation axis L1 relative to the drive shaft support member 2, a rotary drum 5 secured to the drive shaft 4, ten welding units 6 secured to the rotary drum 5, ten power transmission mechanisms 7 (only two of which are shown in FIG. 3) each provided for transmitting a power from the cam drum 3 and a cam follower 23 to a welding unit 6, a slip ring (rotary connector) 8 and a rotary joint 9 provided at a base end of the drive shaft 4, a wire guide member 11 and a tube connecting member 12 provided at a distal end of the drive shaft 4, and a motor 10 for rotationally driving the drive shaft 4.

In the description hereinafter, the direction parallel to the rotation axis L1 in FIG. 3 will be referred to as "X direction", the vertical direction of FIG. 3 will be referred to as Z direction, and the direction perpendicularly intersecting the X-Z plane will be referred to as "Y direction".

Figure 4:
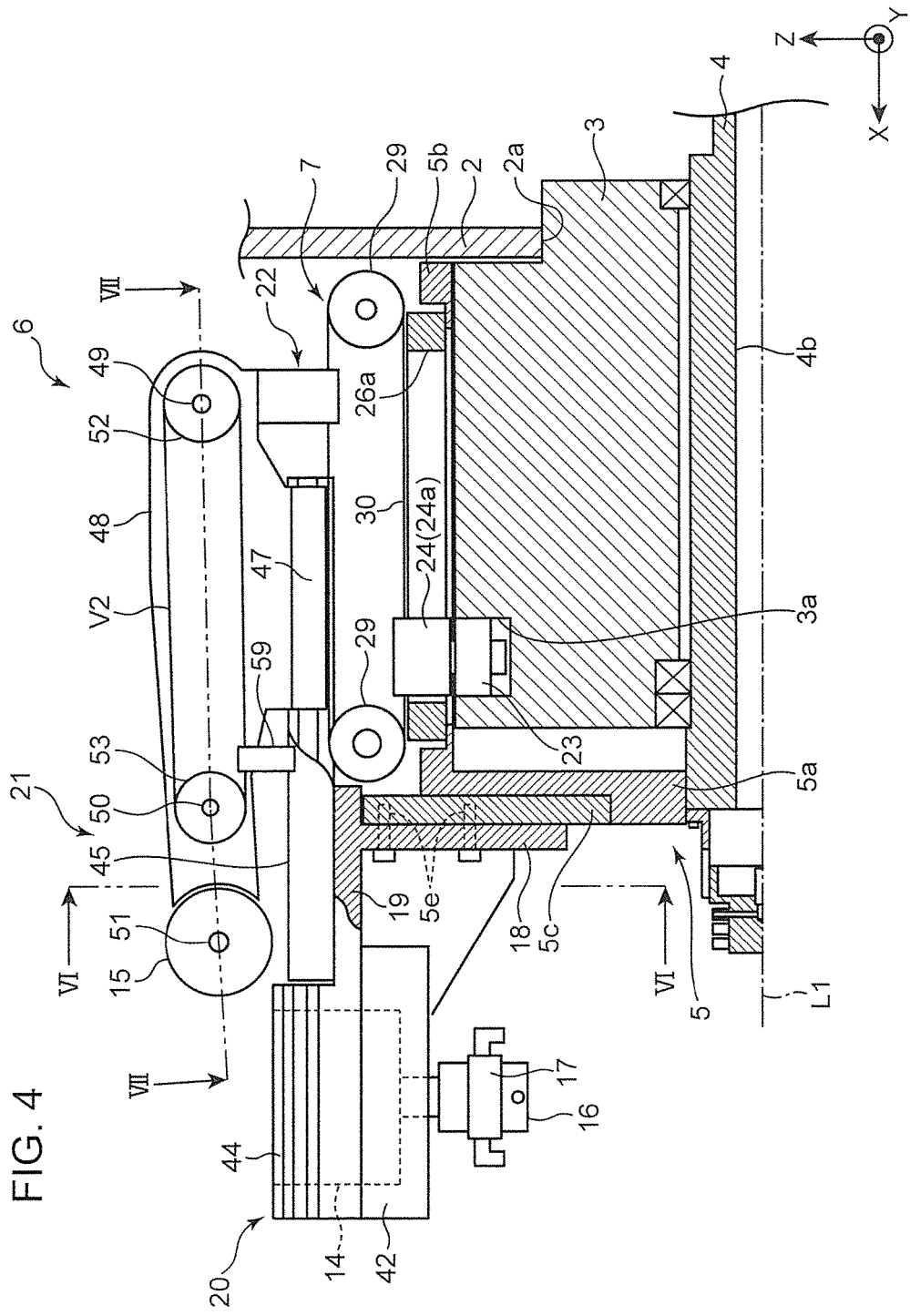
FIG. 4 is an enlarged sectional view of a portion of FIG. 3.

With reference to FIGS. 3 and 4, the drive shaft support member 2 supports the above-described components (excluding the drive shaft support member 2) of the ultrasonic welding device 1 on the work surface. Specifically, the drive shaft support member 2 is in the form of a plate having a through hole 2a passing therethrough in the X direction.

The cam drum 3 is secured to the drive shaft support member 2 with one end in the X direction being fitted in the through hole 2a of the drive shaft support member 2. In this state, an axis of the cam drum 3 coincides with the rotation axis L1.

Further, the cam drum 3 has a circumferential surface formed with the cam groove 3a. The cam groove 3a has a shape that allows the cam followers 23 which revolve about the rotation axis L1 to move in the X direction, as described in detail later. The cam drum 3 and the cam followers 23 correspond to a driving mechanism which drives anvils 15 described later in such a manner that the anvils 15 move relative to horns 14.

The drive shaft 4 is rotationally driven by the motor 10. Specifically, a belt V1 is wound around a pulley 4a provided at an intermediate portion of the drive shaft 4 and a pulley 10a provided at an output shaft of the motor 10. A power of the motor 10 is transmitted to the drive shaft 4 via the belt V1 according to rotation of the output shaft of the motor 10. The motor 1 is secured to the drive shaft support member 2 via an unillustrated bracket.

The drive shaft 4 passes through the cam drum 3 in the X direction in a manner rotatable relative to the cam drum 3. In other words, the drive shaft 4 is indirectly supported on the drive shaft support member 2 via the cam drum 3. The base end of the drive shaft 4 lies on the side of the drive shaft support member 2 opposite to the cam drum 3, and the distal end of the drive shaft 4 lies on the side of the cam drum 3 opposite to the drive shaft support member 2.

The rotary drum 5 includes a disk 5a secured to the distal end of the drive shaft 4, a covering wall 5b extending from the rim of the disk 5a in the X direction and covering the circumferential surface of the cam drum 3, and an adjuster plate 5c detachably attached to the side of the disk 5a opposite to the covering wall 5b. The disk 5a and the adjuster plate 5c correspond to a rotary member which is rotatable about the rotation axis L1.

The adjuster plate 5c is formed with screw holes 5e (see FIG. 4) for attaching the welding units 6.

Hereinafter, with reference to FIGS. 4 to 7, the welding units 6 will be described. Because the ten welding units 6 have the same configuration, description will be made about the configuration of one welding unit 6 shown in FIGS. 4 to 7.

The welding unit 6 includes a horn (second welding tool) 14 and an anvil (first welding tool) 15 for sandwiching the sheet W to thereby weld the sheet W, an ultrasonic wave generator 16 connected to the horn 14, a cooling jacket 17 (cooler) for cooling the ultrasonic wave generator 16, a attaching section 18 for allowing the welding unit 6 to be attached to the rotary drum 5 (adjuster plate 5c), a base 19 connected to an end of the attaching section 18 and extending in the X direction, a horn holding mechanism 20 provided at a distal end of the base 19 and holding the horn 14, and an anvil holding mechanism 21 provided at a base end of the base 19 and holding the anvil 15.

The attaching sections 18 allow, as shown in FIGS. 2 and 3, the welding units 6 to be attached to the rotary drum 5 in a state that the horn holding mechanisms 20 lie on the same circumference about the rotation axis L1. Further, the attaching sections 18 can be attached to the rotary drum 5 (adjuster plate 5c) in such a manner as to allow attaching positions of the welding units 6 to the rotary drum 5 to be adjusted in radial directions (in the Z direction in FIGS. 4 and 6) centered on the rotation axis L1.

Figure 6:
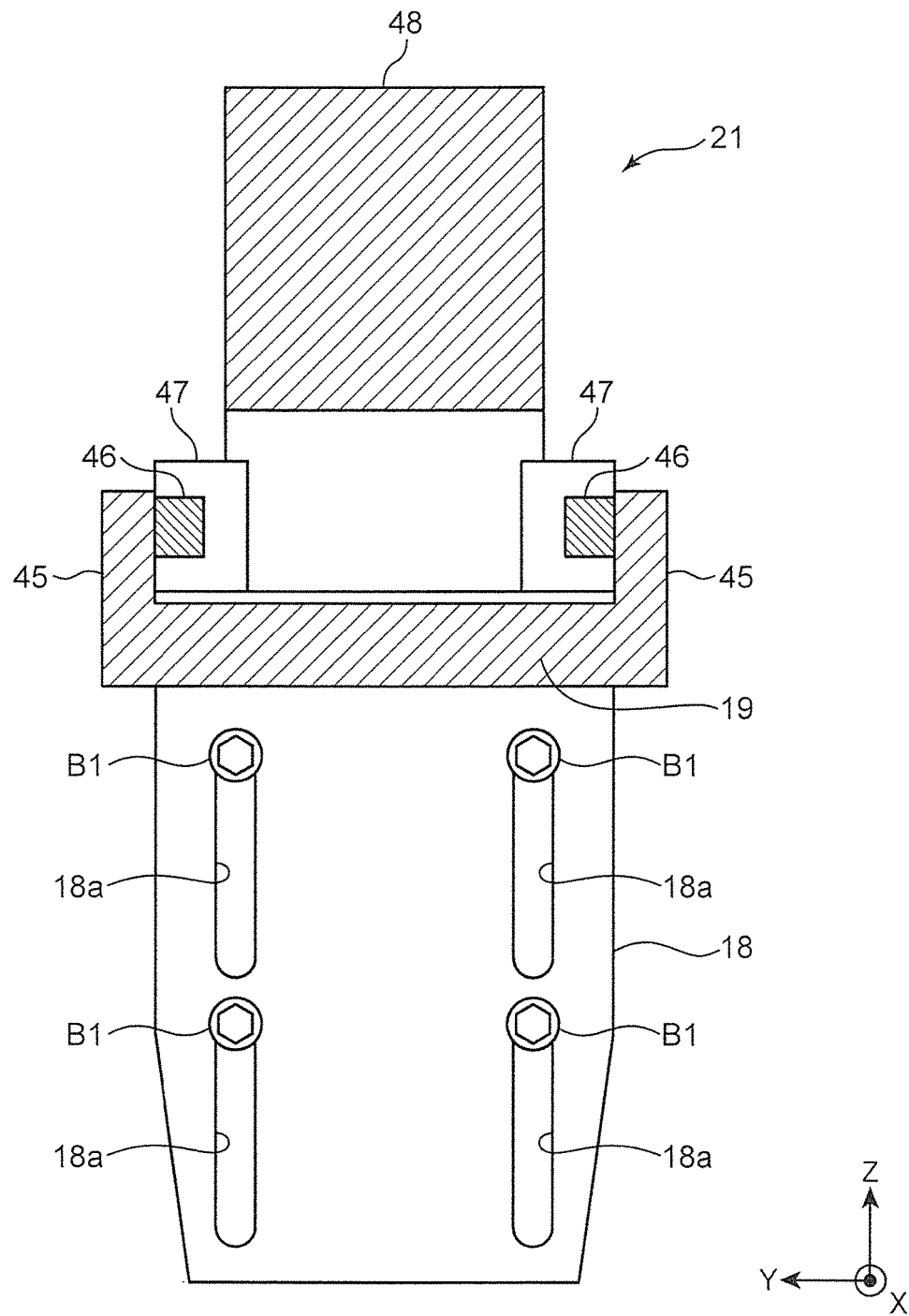
FIG. 6 is a sectional view taken along the line VI-VI in FIG. 4.
Figure 7:
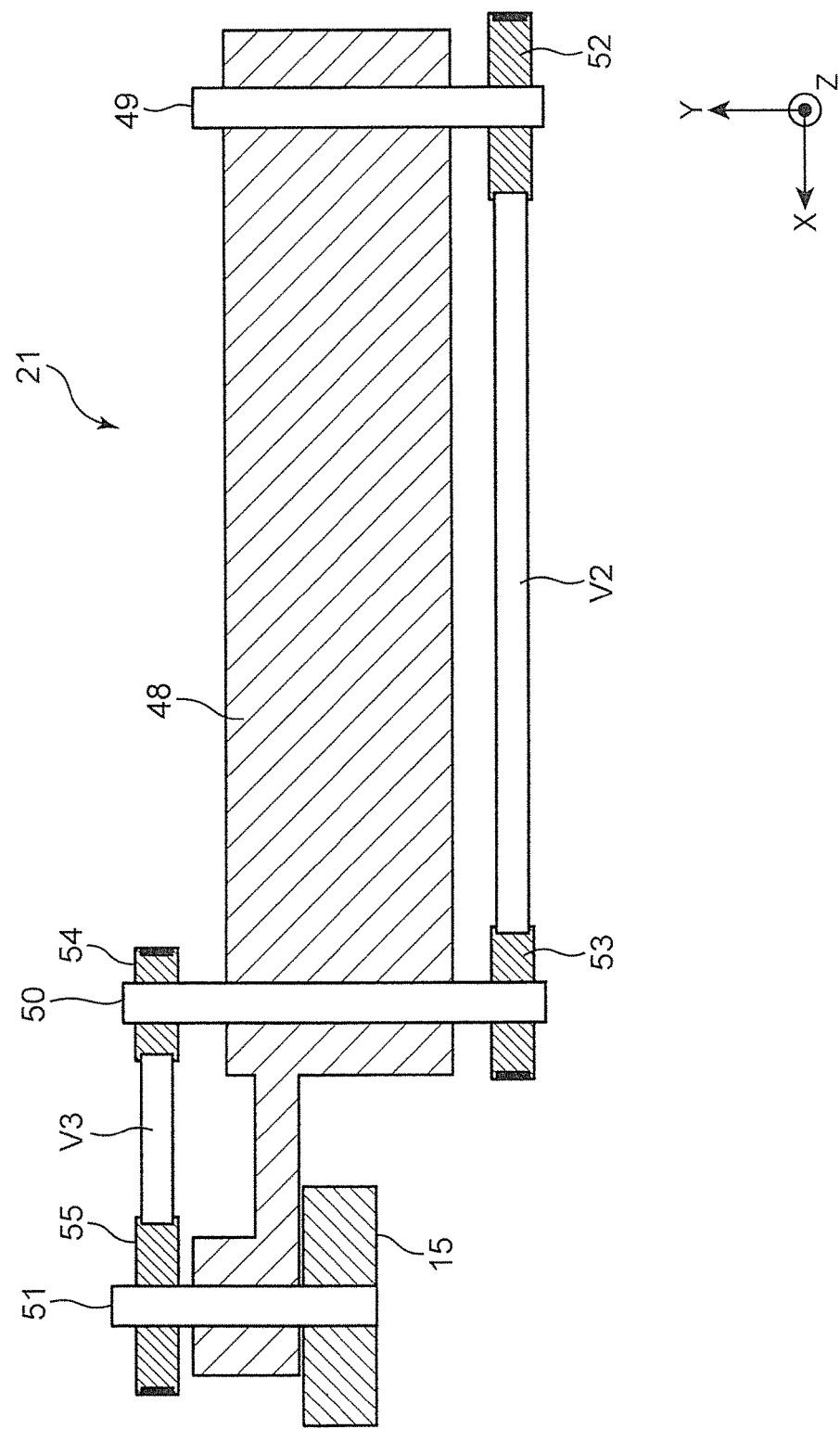
FIG. 7 is a sectional view taken along the line VII-VII in FIG. 4.

Specifically, the attaching section 18 is formed with four long holes 18a extending in the radial direction (in the Z direction in FIG. 6) and passing therethrough in the X direction, as shown in FIG. 6. The attaching section 18 can be attached to the adjuster plate 5c by inserting bolts B1 into the long holes 18a and screwing the bolts B1 into screw holes 5e of the adjuster plate 5c. Further, a attaching position of the attaching section 18 (welding unit 6) can be adjusted in the radial direction by loosening the bolts B1 and moving the attaching section 18 in the radial direction and then screwing the bolts B1 into the screw holes 5e again.

In the case that the attaching position of the attaching section 18 needs to be adjusted beyond the range of the long hole 18a, the adjustment range of the attaching position of the welding unit 6 can be expanded by attaching an alternative adjuster plate 5c to the disk 5a, the alternative adjuster plate 5c having screw holes 5e formed at different positions in the radial direction.

Figure 5:
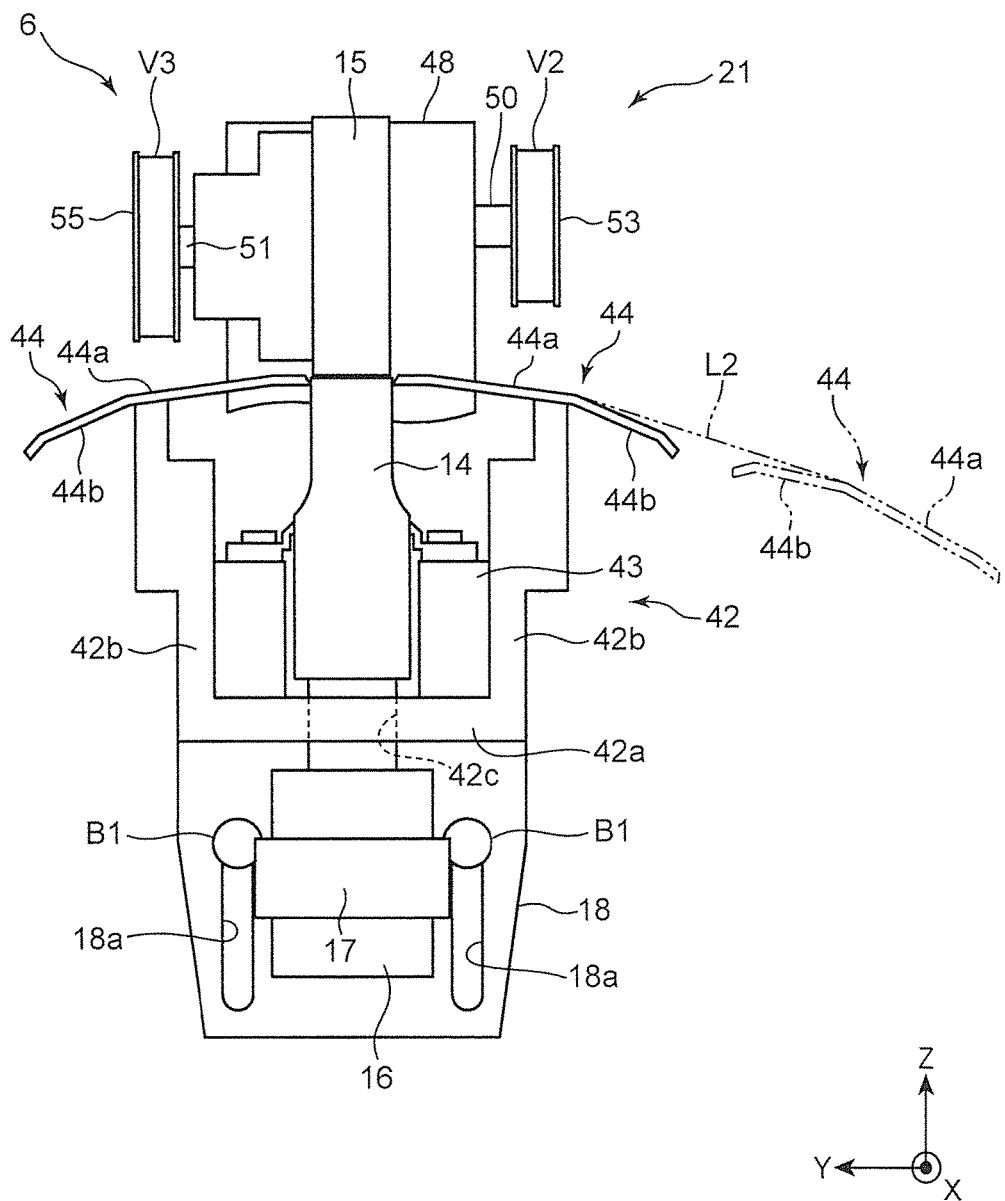
FIG. 5 is a front view showing a horn holding mechanism shown in FIG. 4.

With reference to FIGS. 4 and 5, the horn holding mechanism 20 supports the horn 14 with the horn 14 being exposed radially outward.

Specifically, the horn holding mechanism 20 includes a covering member 42 covering the horn 14 from one side (lower side in FIGS. 4 and 5) of the horn 14 in a radial direction and from both sides of the horn 14 in the Y direction, a horn support member 43 disposed inside the covering member 42 and supporting the horn 14, and a pair of sheet support members (object support members) 44 secured to the covering member 42.

The covering member 42 includes a bottom plate 42a, and a pair of side plates 42b standing on opposite end portions of the bottom plate 42a in the Y direction. The bottom plate 42a is formed with a through-hole 42c passing therethrough in the Z direction. The ultrasonic wave generator 16 disposed radially inside the covering member 42 is connected to the horn 14 through the insertion hole 42c.

The horn support member 43 is secured to the covering member 42 and supports an intermediate portion (a portion corresponding to a node of vibration transmitted from the ultrasonic wave generator 16) of the horn 14. A width dimension of the horn 14 in the X direction corresponds to a width (see FIG. 1) of the welding range D1 of the weld section S formed in the sheet W.

The sheet support members 44 are respectively attached to end surfaces of the side plates 42b in such a manner that the sheet support members 44 extend on both sides of a distal end of the horn 14 in a direction along the circumference about the rotation axis L1. Specifically, each sheet support member 44 includes a support portion 44a extending in the circumferential direction from the horn 14, and a bending portion 44b extending at an angle from a circumferential end portion. The disk 5a and the adjuster plate 5c of the rotary drum 5, the attaching sections 18, and the sheet support members 44 correspond to a rotary support mechanical assembly which is rotatable about the rotation axis L1 and operable to support the sheet W over a circumference centered on the rotation axis L1, the sheet W being continuously supplied.

The support portion 44a has a radially outer surface which serves as a support surface for supporting the sheet W. Specifically, a width dimension of the support portion 44a in the X direction corresponds to a width dimension D2 (see FIG. 1) between a waist side end portion and a crotch section side end portion of the sheet W.

The bending portion 44b extends at an angle from a distal end of the support portion 44a and lies on the rotation axis L1 side of a straight line L2, the line L2 connecting distal end portions of adjacent support portions 44a, as shown in FIG. 5.

As a result, each portion of the sheet W (see FIG. 1) that includes the weld section S can be supported by the support portions 44a and the distal end of the horn 14, and each portion of the sheet W that includes the absorber A thicker than the weld section S can be disposed between adjacent bending portions 44b. Therefore, it is possible to prevent the portion of the sheet W exclusive of the absorbers A from rising due to the thickness of the absorbers A, unlike the case where the sheet W is supported on the same surface.

Further, the positions of the sheet support members 44 can be shifted by adjusting the above-mentioned attaching positions of the attaching sections 18 to the adjuster plate 5c. Specifically, for example, it is possible to increase the length (circumference) of the sheet W that can be supported by the sheet support members 44 by changing the attaching positions of the horn holding mechanisms 20 attached by means of the attaching sections 18 to radially outward positions centered on the rotation axis L1, as shown by the double dashed line in FIG. 8.

Thus, the attaching sections 18 and the adjuster plate 5*c* correspond to an attaching mechanism that allows the plurality of sheet support members 44 to be attached to the rotary drum 5 in a state that the sheet support members 44 lie on the same circumference about the rotation axis L1 and that allows the attaching positions of the sheet support members 44 to the rotary drum 5 to be adjusted in the radial directions centered on the rotation axis L1.

With reference to FIGS. 4 to 7, the anvil holding mechanism 21 holds the anvil 15 in such a manner that the anvil 15 is movable relative to the horn holding mechanism 20 (the horn 14) in the X direction.

Specifically, the anvil holding mechanism 21 includes a pair of rail holding plates 45 standing on the base 19 and facing each other in the Y direction, a pair of rails 46 respectively held by the rail holding plates 45, a pair of sliders 47 respectively engageable with the rails 46 in a manner movable in the X direction, a main body 48 fixedly holding the sliders 47, three rotary shafts 49 to 51 provided in the main body 48, four timing pulleys 52 to 55 rotatable about the rotary shafts 49 to 51, respectively, timing belts V2 and V3 wound around the timing pulleys 52 to 55, and a connection member (see FIG. 4) 59 connecting the timing belt V2 and the rail holding plates 45.

The main body 48 is attached to the rail holding plates 45 (the base 19) in a manner movable in the X direction owing to the engagement between the rails 46 and the sliders 47.

The rotary shafts 49 to 51 each extend in the Y direction, the rotary shafts being arranged in the X direction and rotatable about an axis parallel to the Y direction relative to the main body 48. The timing pulley 52 is provided at one end of the rotary shaft 49. The timing pulley 53 is provided at one end portion of the rotary shaft 50 that is on the same side as the timing pulley 52, and the timing pulley 54 is provided at the other end portion of the rotary shaft 50 opposite to the timing pulley 53. The timing pulley 55 is provided at one end portion of the rotary shaft 51 that is on the same side as the timing pulley 54, and the anvil 15 is provided at the other end portion of the rotary shaft 51 opposite to the timing pulley 55.

The timing belt V2 is wound around the timing pulley 52 and the timing pulley 53. The timing belt V3 is wound around the timing pulley 54 and the timing pulley 55. The connection member 59 connects a specific portion of the timing belt V2 and the rail holding plates 45, the specific portion of the timing belt V2 lying on a side of the rotation axis L1 side with respect to the timing pulleys 52 and 53.

In the movement of the main body 48 in the X direction relative to the rail holding plates 45 (the base 19), the power to move the timing belt V2 in the X direction is transmitted from the rail holding plates 45 through the connection member 59. As a result, the timing pulleys 52 and 53 rotate, and the rotation of the timing pulley 53 rotates the timing pulley 54. Consequently, the timing belt V3 moves to rotate the timing pulley 55, which in turn rotates the anvil 15.

In other words, the anvil 15 rotates in response to moving in the X direction relative to the horn 14. Thus, when the anvil 15 is reciprocatively moved relative to the horn 14, it is possible to bring the same position of an outer surface of the anvil 15 into contact with the same position of the sheet W in the forward stroke and the backward stroke of the reciprocation of the anvil 15. Therefore, in the case that a predetermined weld pattern is formed on the outer surface of the anvil 15, it is possible to reliably form a weld section corresponding to the weld pattern on the sheet W.

Figure 9:
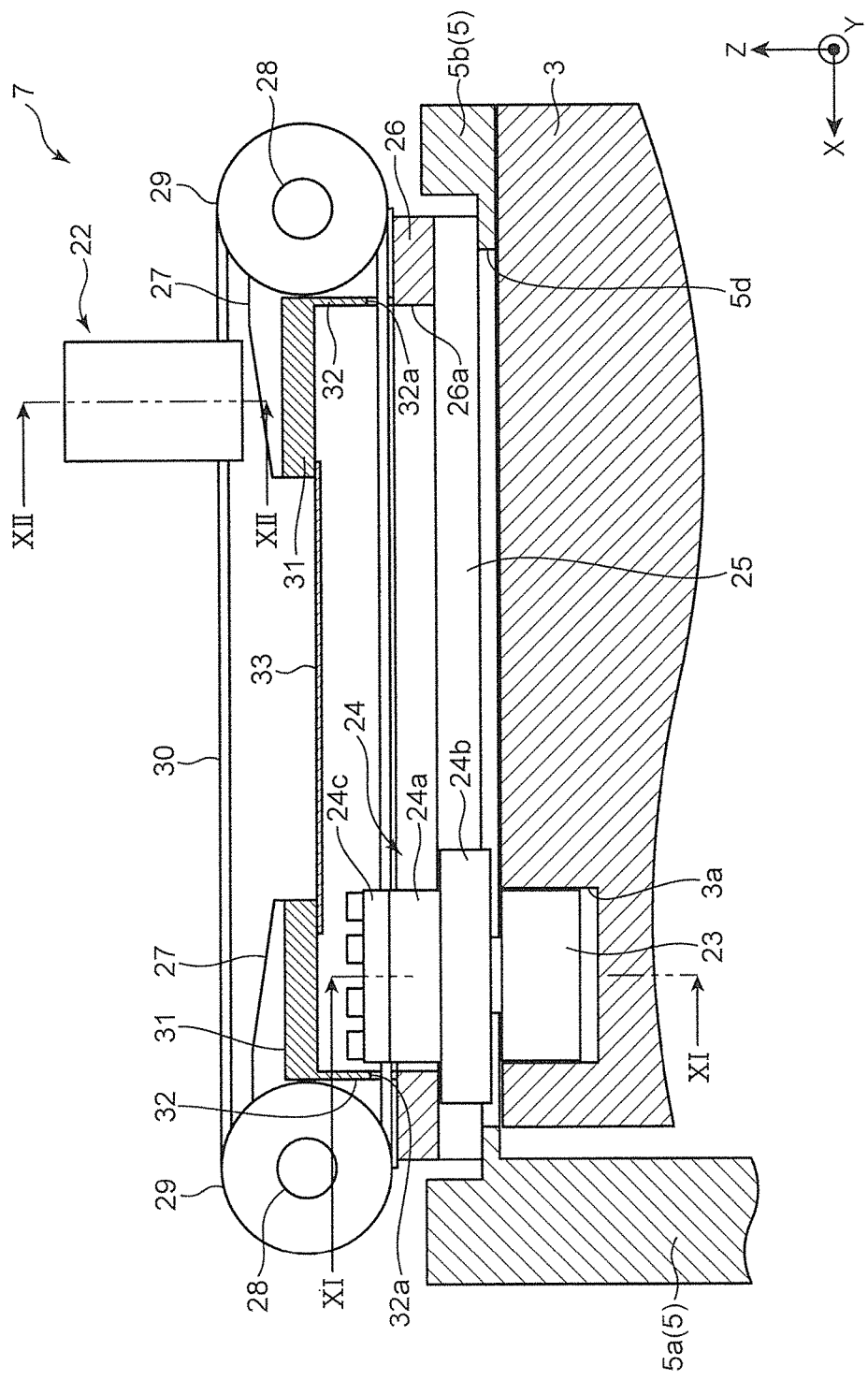
FIG. 9 is an enlarged sectional side view of a power transmission mechanism shown in FIG. 4.

With reference to FIGS. 4 and 9, the power transmission mechanisms 7 are attached to a circumferential surface of the covering wall 5*b* of the rotary drum 5. The covering wall 5*b* is formed with a long hole 5*d* for allowing the cam followers 23 to move along the cam groove 3*a*.

Figure 10:
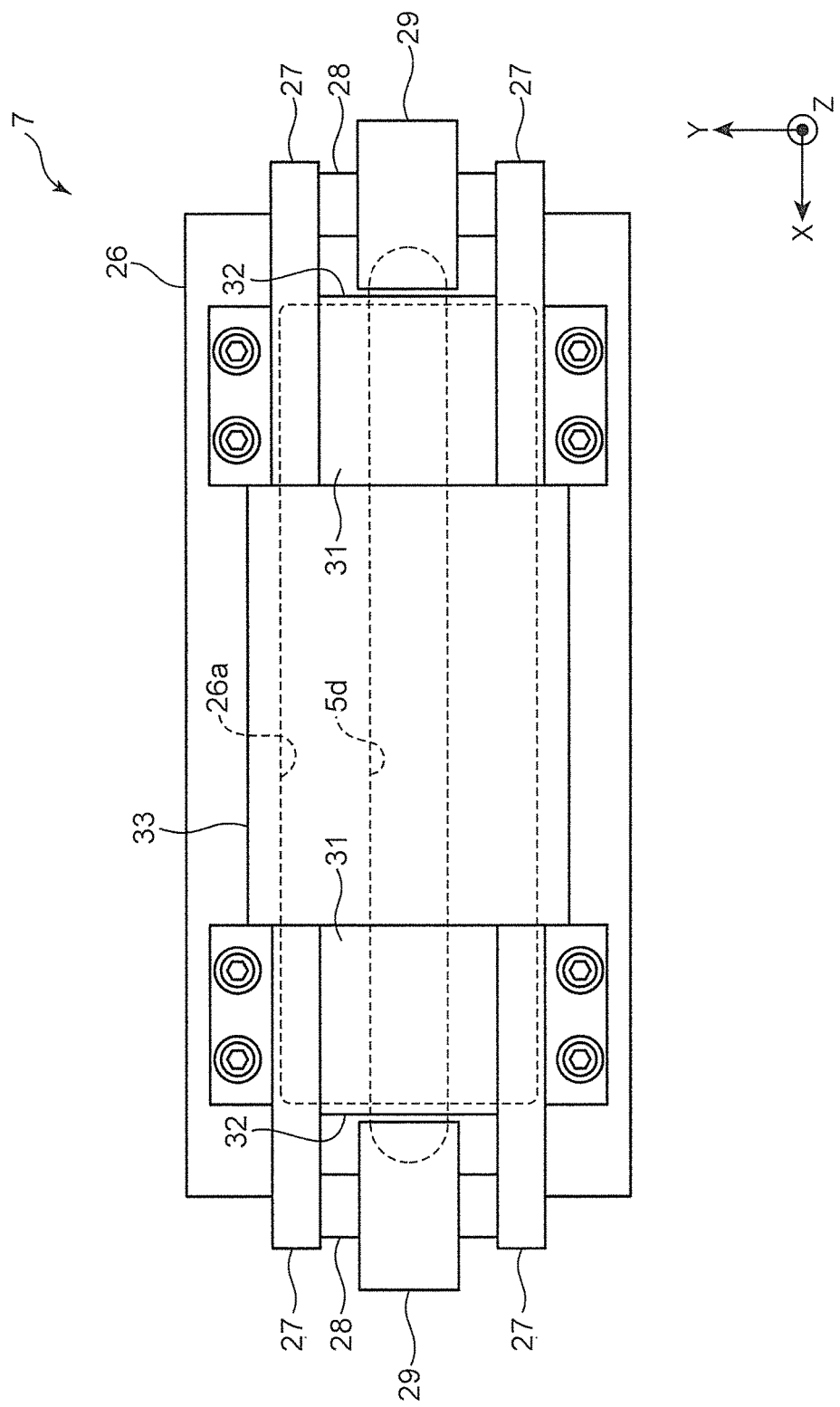
FIG. 10 is a plan view of the power transmission mechanism shown in FIG. 9.
Figure 11:
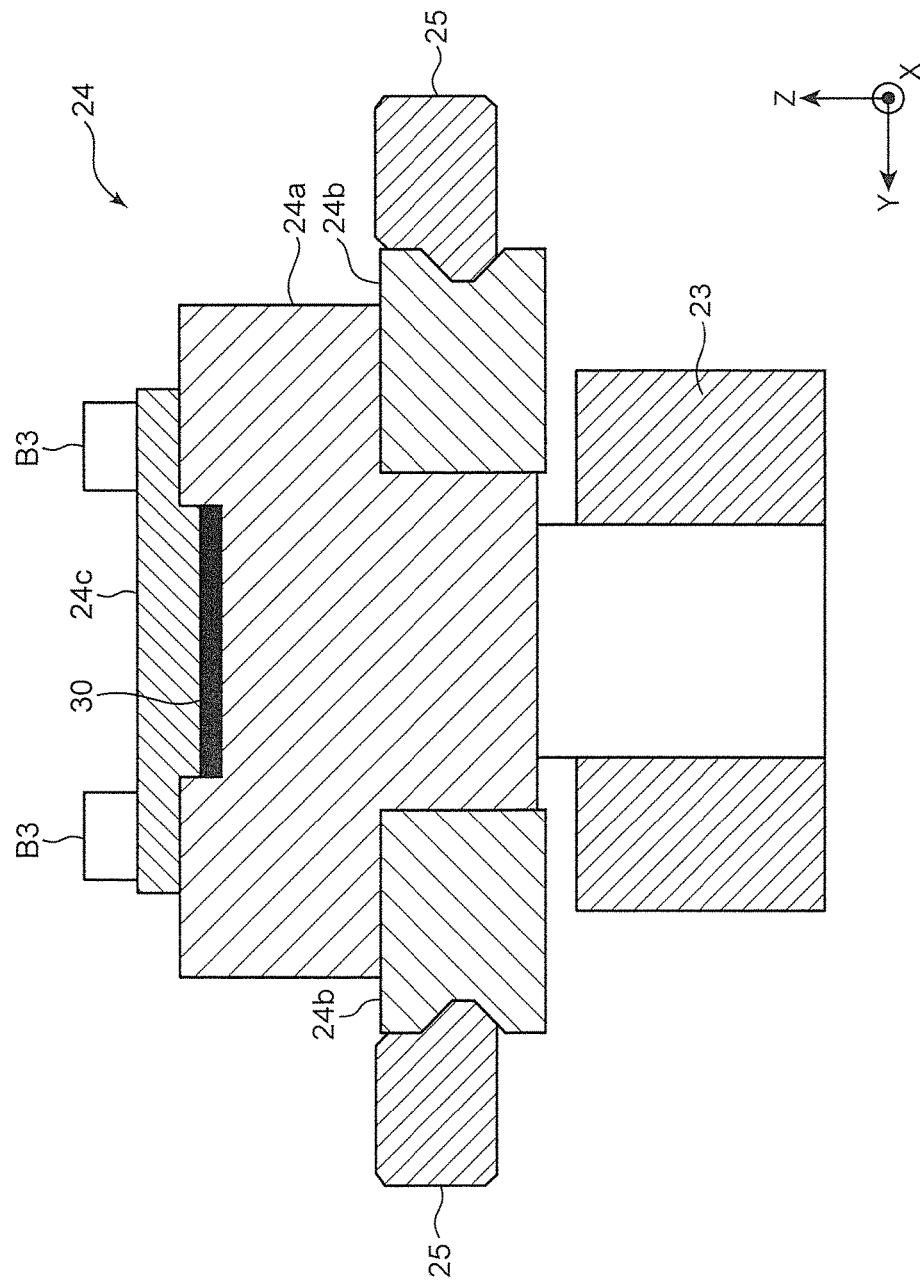
FIG. 11 is a sectional view taken along the line XI-XI in FIG. 9.

The power transmission mechanism 7 includes, as shown in FIGS. 9 to 11, a holding member 24 holding the cam follower 23, rails 25 supporting the hold member in such a manner that the holding member is movable in the X direction, a base 26 disposed on the rails 25, four brackets 27 standing on the base 26, a pair of timing pulleys 29 supported in a manner rotatable about support shafts 28 extending between the brackets 27, a timing belt (endless belt) 30 wound around the timing pulleys 29, and a connection mechanism 22 connected to the above-mentioned main body 48 of the anvil holding mechanism 21.

The holding member 24 includes, as shown in FIG. 11, a holding member body 24*a* secured to the cam follower 23, sliders 24*b* attached to opposite side surfaces of the holding member body 24*a* in the Y direction, and a clamping piece 24*c* for sandwiching the timing belt 30 in cooperation with the holding member body 24*a*.

The weight of the cam follower 23 and the holding member 24 secured to the cam follower 23 is preferably equal to, but may be lighter than the weight of the main body 48 including the anvil 15. As described later, the cam follower 23 and the holding member 24 move in an opposite direction to the anvil 15 to thereby function as a weight which reduces vibration caused by the movement of the anvil 15.

The sliders 24*b* are engaged with the rails 25 in a manner movable in the X direction.

Bolts B3 are screwed into unillustrated screw holes formed in the holding member body 24*a* to thereby allow the clamping piece 24*c* to hold the timing belt 30 by sandwiching it in cooperation with the holding member body 24*a*.

The base 26 includes a through hole 26*a* passing the base 26 in the Z direction, and the holding member 24 is inserted in the through hole 26*a* in a manner movable in the X direction.

With reference to FIGS. 9 and 10, two of the brackets 27 are disposed on one side of the base 26 in the X direction and face each other in the Y direction, and the other two of the brackets 27 are disposed on the other side of the base 26 in the X direction and face in the Y direction. The support shafts 28 extending in the Y direction are each provided between two facing brackets 27, and the timing pulleys 29 are respectively provided at the support shafts 28.

The above-mentioned holding member 24 is connected to a specific portion of the timing belt 30 that is on the side of the timing pulleys 29 closer to the rotation axis L1. The connection mechanism 22 is connected to a specific portion of the timing belt 30 that is on the side of the timing pulleys 29 farther from the rotation axis L1.

As shown in FIG. 12, the connection mechanism 22 includes a pair of a first clamping member 57 and a second clamping member 58 which sandwich the timing belt 30, and a connection plate 56 provided for connecting the first clamping member 57 and the above-mentioned main body 48 of the anvil holding mechanism 21.

The first clamping member 57 includes an attached portion 57*a* for allowing the connection plate 56 to be attached thereto, the attached portion 57*a* having an insertion hole 57*b* passing therethrough in the Y direction. On the other hand, the above-mentioned main body 48 of the anvil holding mechanism 21 includes an attached portion 48a for allowing the connection plate 56 to be attached thereto, the attached portion 48a having an insertion hole 48b passing therethrough in the Y direction.

The connection plate 56 includes a pair of screw holes 56a for allowing bolts B2 that are respectively inserted in the insertion hole 57b of the first clamping member 57 and the insertion hole 48b of the main body 48 to be screwed therein. Therefore, it is possible to connect the timing belt 30 and the anvil holding mechanism 21 via the connection plate 56 by screwing the bolts B2 into the screw holes 56a.

Figure 8:
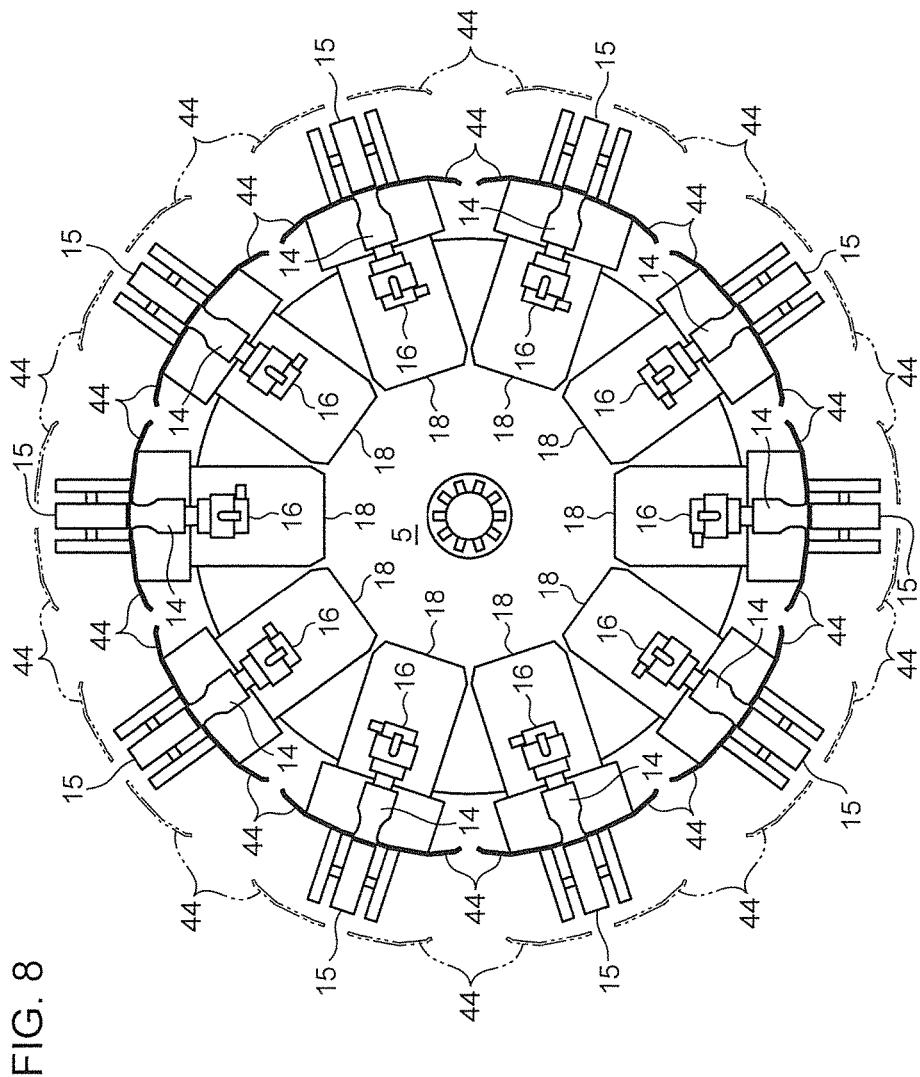
FIG. 8 is a diagram corresponding to FIG. 2, FIG. 8 illustrating adjusted attaching positions of sheet support members.

As described above, the attaching positions of the welding units 6 can be adjusted in radial directions centered on the rotation axis L1 by shifting the attaching positions of the attaching sections 18 along the long holes 18a (see FIGS. 6 and 8). When the attaching positions of the welding units 6 are changed, the distance between the timing belt 30 and the anvil holding mechanisms 21 is changed in the radial directions. Therefore, by preparing an adjustment connection plate 56A that have screw holes 56a disposed at a different interval from the holes of the connection plate 56 in advance, it is possible to connect the timing belt 30 and the anvil holding mechanisms 21 even after the adjustment of the attaching positions of the welding units 6.

The cam follower 23 and the anvil holding mechanism 21 are thus connected by the power transmission mechanism 7 to thereby allow the anvil 15 and the weight (the cam follower 23 and the holding member 24) to move as follows.

With reference to FIGS. 3 and 9, when the drive shaft 4 (motor 10) is rotationally driven to rotate the rotary drum 5 relative to the cam drum 3, the cam follower 23 moves in the X direction along the cam groove 3a.

The cam follower 23 and the holding member 24 supporting the cam follower 23 move in the X direction together. On the other hand, the connection mechanism 22 connected to the holding member 24 via the timing belt 30, i.e. the anvil holding mechanism 21, moves in the opposite direction to the cam follower 23 and the holding member 24 in the X direction.

Thus, the timing belt 30 and the timing pulleys 29 correspond to a power distribution mechanism.

This allows the weight (the cam follower 23 and the holding member 24) and the anvil holding mechanism 21 (anvil 15) to synchronously move in the opposite directions. Therefore, it is possible to reduce vibration caused by movement of the anvil 15.

Here, the range of movement of the anvil 15 is determined by the cam groove 3a, as follows.

The anvil 15 is movable within a movable range between an initial position (the upper position shown in FIG. 3) shifted from the horn 14 on a side of the cam drum 3 in the X direction and a intermediate position (the lower position shown in FIG. 3) shifted from the horn 14 on an opposite side to the cam drum 3 in the X direction.

Further, the relationship between rotational positions about the rotation axis L1 and the movement positions of the anvil 15 is determined by the cam groove 3a, as follows.

As shown in FIG. 2, the feed-in roller F1 and the feed-out roller F2 are disposed between a rotational position R1 and a rotational position R9 centered on the rotation axis L1. The angle between the rotational position R1 and the rotational position R9 is 36 degrees. The anvil 15 is disposed at the initial position (the upper position shown in FIG. 3) in an extent from the rotational position R9 to the rotational position R1.

In an extent from the rotational position R1 to a rotational position R2, the anvil 15 accelerates from the initial position toward the intermediate position (hereinafter, the direction of this movement will be referred to as "forward"). The angle between the rotational position R1 and the rotational position R2 is 36 degrees.

In an extent from the rotational position R2 to a rotational position R4, the anvil 15 moves forward at a constant speed. During this movement, the sheet W is welded between the horn 14 and the anvil 15. The angle between the rotational position R2 and the rotational position R4 is 108 degrees.

In an extent from the rotational position R4 to a rotational position R5, the anvil 15 decelerates (the anvil 15 is imparted with a backward acceleration) to stop at the intermediate position (the lower position shown in FIG. 3) when it reaches the rotational position R5. The angle between the rotational position R4 and the rotational position R5 is 18 degrees.

In an extent from the rotational position R5 to a rotational position R6, the anvil 15 accelerates backward from the intermediate position toward the initial position. The angle between the rotational position R5 and the rotational position R6 is 18 degrees.

In an extent from the rotational position R6 to a rotational position R8, the anvil 15 moves backward at a constant speed. During this movement, the sheet W is welded again between the horn 14 and the anvil 15. The angle between the rotational position R6 and the rotational position R8 is 108 degrees.

In an extent from the rotational position R8 to a rotational position R9, the anvil 15 decelerates (the anvil 15 is imparted with a forward acceleration) to stop at the initial position when it reaches the rotational position R9. The angle between the rotational position R8 and the rotational position R9 is 36 degrees.

In the present embodiment, two anvils 15 provided at symmetric positions by 180 degrees around the rotation axis L1 do not synchronously move in opposite directions especially during the acceleration and deceleration.

Here, for example, if the movement timings of the anvils 15 to the rotational positions are so set that two anvils 15 provided at symmetric positions by 180 degrees apart around the rotation axis L1 synchronously move in opposite directions, it is possible to reduce vibration of the ultrasonic welding device 1 as a whole, with or without the above-mentioned weights (the cam followers 23 and the holding members 24).

In this case, the relationship between the rotational positions about the rotation axis L1 and the movement positions of the anvil 15 can be set by the cam groove 3a, as follows.

In an extent from the rotational position R1 to the rotational position R2 shown in FIG. 2, the anvil 15 accelerates forward, and in an extent from the rotational position R2 to the rotational position R3, the anvil 15 is caused to move forward at a constant speed. The angle between the rotational position R2 and the rotational position R3 is 72 degrees.

In an extent from the rotational position R3 to the rotational position R4, the anvil 15 decelerates to stop at the intermediate position when it reaches the rotational position R4. The angle between the rotational position R3 and the rotational position R4 is 36 degrees.

In an extent from the rotational position R4 to the rotational position R6, the anvil 15 stops at the intermediate position. Consequently, one anvil 15 that rotates from the rotational position R9 to the rotational position R1 (to stop at the initial position) and another anvil 15 that rotates from the rotational position R4 to the rotational position R6 (to stop at the intermediate position) synchronously move in the opposite directions.

In an extent from the rotational position R6 to the rotational position R7, the anvil 15 accelerates backward from the intermediate position. The angle between the rotational position R6 and the rotational position R7 is 36 degrees.

In an extent from the rotational position R7 to the rotational position R8, the anvil 15 moves backward at a constant speed. The angle between the rotational position R7 and the rotational position R8 is 72 degrees.

Thereafter, in an extent from the rotational position R8 to the rotational position R9, the anvil 15 decelerates to stop at the initial position when it reaches the rotational position R9.

This configuration allows two anvils 15 provided at symmetric positions by 180 degrees apart around the rotation axis L1 to synchronously move in the opposite directions, which makes it possible to reduce vibration of the ultrasonic welding device 1 as a whole. Furthermore, the above-described configuration in which the weights (the cam followers 23 and the holding members 24) are caused to move in the opposite direction to the anvils 15 also makes it possible to reduce vibration in each welding unit 6. Therefore, the vibration of the ultrasonic welding device 1 as a whole can be more effectively reduced.

In contrast, in the present embodiment, two anvils 15 provided at symmetric positions by 180 degrees do not synchronize in the opposite directions, which, however, allows the anvils 15 to stop only for a short time. Owing to this, the period for welding the sheet W can be set long.

Again, with reference to FIGS. 9 and 10, the power transmission mechanism 7 is attached to the covering wall 5b of the rotary drum 5 in a state where the power transmission mechanism 7 covers the long hole 5d.

Specifically, the power transmission mechanism 7 includes a pair of ceiling plates 31 and a pair of side plates 32 disposed between the above-mentioned brackets 27, and a covering plate 33 disposed between the ceiling plates 31.

The above-mentioned base 26 covers opposite end portions of the long hole 5d of the covering wall 5b in the X direction and exposes a middle portion of the long hole 5d through the through hole 26a. The ceiling plates 31, the side plates 32 and the covering plate 33 cover the portion of the long hole 5d that is exposed through the through hole 26a.

Specifically, the pair of side plates 32 stand respectively on opposite end portions of the base 26 in the X direction. Each side plate 32 is formed with a through hole 32a for allowing the timing belt 30 to pass therethrough.

The ceiling plates 31 respectively extend from end portions of the side plates 32 in directions toward each other (in the X direction).

The long hole 5d (the through hole 26a of the base 26) is thus covered, thereby making it possible to prevent entry of foreign matter into the long hole 5d.

The base 26, the brackets 27, the ceiling plates 31, the side plates 32, and the covering plate 33 correspond to a holding mechanism that is attached to the covering wall 5b in a state where the holding mechanism covers the long hole 5d, the holding mechanism holding the timing belt 30 and the timing pulleys 29.

Hereinafter, with reference to FIGS. 3, 13 and 14, a configuration for supplying power and cooling air to the ultrasonic wave generators 16 and the cooling jackets 17 will be described.

Figure 14:
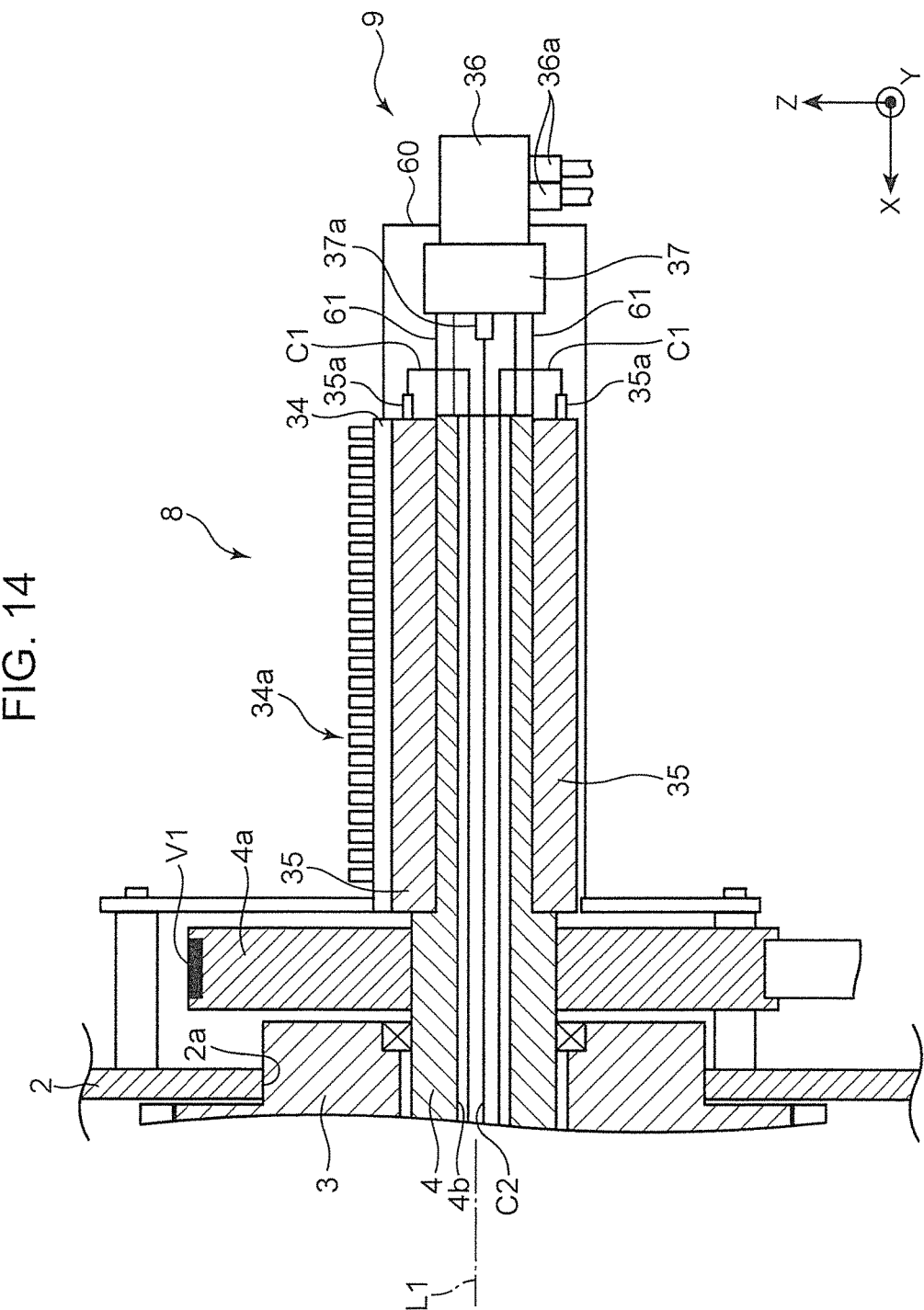
FIG. 14 is an enlarged sectional side view of a base end configuration shown in FIG. 3.

The slip ring 8 allows electrical connection of an unillustrated power source to the ultrasonic wave generators 16 that revolve about the rotation axis L1, as shown in FIGS. 3 and 14. Specifically, the slip ring 8 includes a stationary terminal holding portion 34 secured to the drive shaft support member 2, and a rotary cylinder portion 35 rotatable about the rotation axis L1 relative to the stationary terminal holding portion 34.

The stationary terminal holding portion 34 includes a plurality of stationary terminals 34a electrically connected to the unillustrated power source. The rotary cylinder portion 35 includes a plurality of rotary terminals 35a which remain electrically connected to the plurality of stationary terminals 34a even while rotating relative to the stationary terminal holding portion 34. The stationary terminals 34a are electrically connected to the rotary terminals 35a in one-to-one correspondence. Specifically, the stationary terminal holding portion 34 includes conductive contact parts (unillustrated) electrically connected to the stationary terminals 34a, and the rotary cylinder portion 35 includes contact parts (unillustrated) electrically connected to the rotary terminals 35a. The rotary cylinder portion 35 is rotatable relative to the stationary terminal holding portion 34 with the respective contact parts being connected to each other. A wire C1 is connected to each rotary terminal 35a, the wires C1 being respectively connected to the ultrasonic wave generators 16. The plurality of stationary terminals 34a constitute a stationary connected portion and the plurality of rotary terminals 35a constitute a rotary connected portion.

The rotary joint 9 allows connection of an unillustrated air source to the cooling jackets 17 that revolve about the rotation axis L1. Specifically, the rotary joint 9 includes a stationary body 36 secured to the drive shaft support member 2 via a cover 60, and a rotary body 37 secured to the drive shaft 4 and rotatable about the rotation axis L1 relative to the stationary body 36.

The stationary body 36 is secured to the stationary terminal holding portion 34 of the slip ring 8 via the cover 60. The stationary body 36 includes a stationary connection portion 36a connected to the unillustrated air source. The rotary body 37 is secured to the rotary cylinder portion 35 of the slip ring 8 via a support 61. The rotary body 37 includes a rotary connection portion 37a which remains connected to the stationary connection portion 36a even while rotating relative to the stationary body 36. Specifically, the stationary body 36 includes a passage (unillustrated) connecting with the stationary connection portion 36a, and the rotary body 37 includes a passage (unillustrated) connecting with the rotary connection portion 37a. The rotary body 37 is rotatable relative to the stationary body 36 in the state that the respective passages communicate with each other. An air tube C2 is connected to the rotary connection portion 37a.

Figure 13:
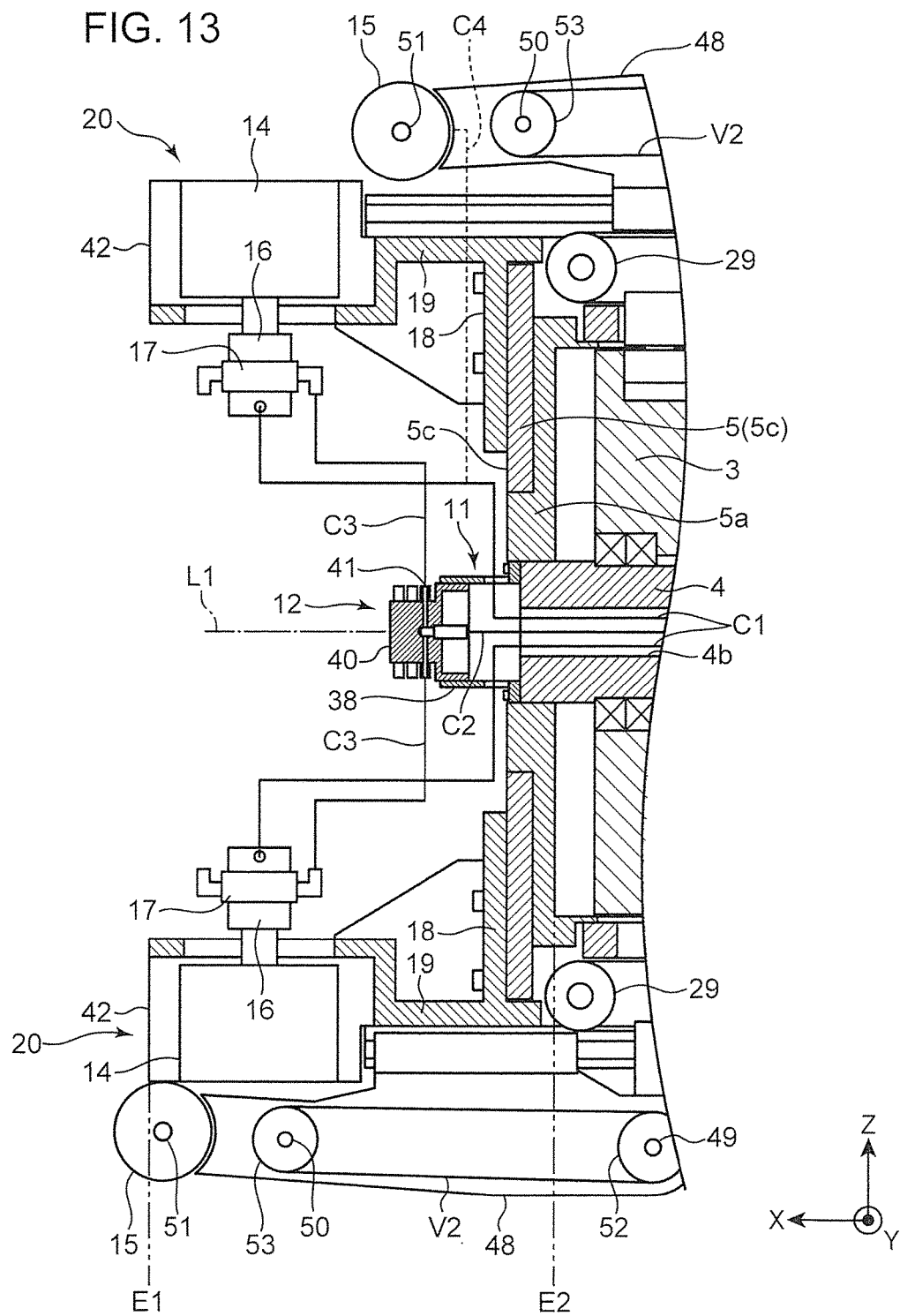
FIG. 13 is an enlarged sectional side view of a distal end configuration shown in FIG. 3.

As shown in FIGS. 13 and 14, the wires C1 and the air tube C2 run from the base end to the distal end of the drive shaft 4 through a through hole 4b which passes through the drive shaft 4 along the rotation axis L1.

Here, the distal end of the drive shaft 4 lies between a distal end E1 and a base end E2 of the rotary support mechanical assembly (the disk 5a, the adjuster plate 5c, the attaching sections 18, and the sheet support members 44).

A wire guide member 11 and a tube connection member 12 are disposed at the distal end of the drive shaft 4.

The wire guide member 11 guides the wires C1 drawn out from the distal end of the drive shaft 4 respectively to the ten ultrasonic wave generators 16, which are the destinations of the wires C1. The wire guide member 11 lies between the distal end E1 and the base end E2 of the rotary support mechanical assembly.

Figure 15:
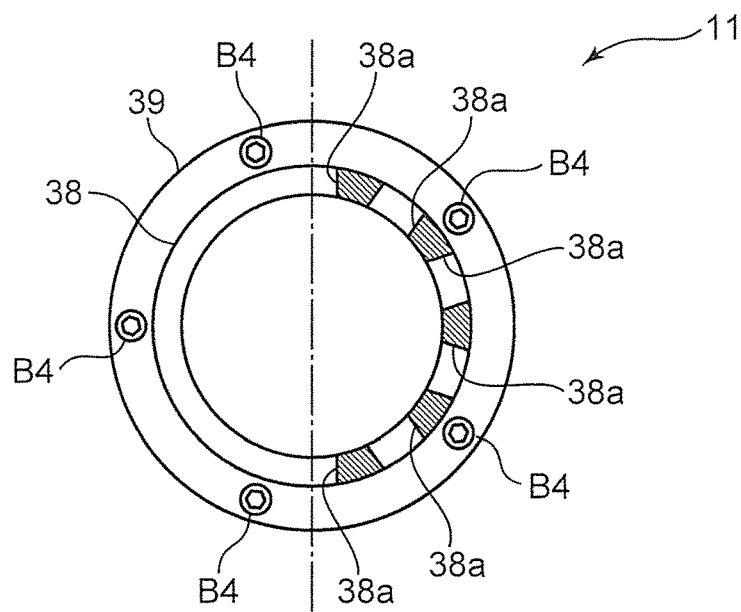
FIG. 15 is a front view of a wire guide member shown in FIG. 13, one-half being shown in section.

Specifically, the wire guide member 11 includes, as shown in FIG. 15, a guide member body 38 in the form of a cylinder, and a stationary portion 39 projecting radially outward from a base end portion of the guide member body 38 and secured to the drive shaft 4 by bolts 4B.

The guide member body 38 is formed with ten guide holes 38a disposed at positions corresponding to the ultrasonic wave generators 16 in a direction along the circumference about the rotation axis L1. The guide holes 38a are formed only over a region extending from a base end portion to an intermediate portion of the guide member body 38 along the rotation axis L1. The wires C1 are guided to the ultrasonic wave generators 16, i.e. the destinations of the wires C, through the guide holes 38a.

The tube connection member 12 is connected to the air tube C2 drawn out from the distal end of the drive shaft 4, the tube connection member 12 being provided to guide air supplied from the air tube C2 into branched air tubes C3. Thus, the tube connection member 12 and the air tubes C2 and C3 correspond to an air circuit that connects the cooling jackets 17 and the rotary connection portion 37a of the rotary joint 9. The tube connection member 12 lies between the distal end portion E1 and the base end portion E2 of the rotary support mechanical assembly.

Figure 16:
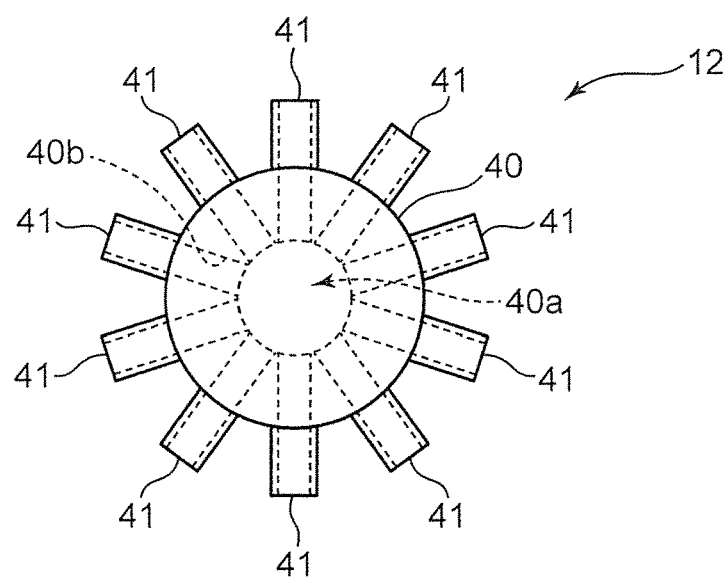
FIG. 16 is a front view of a tube connecting member shown in FIG. 13.

Specifically, the tube connection member 12 includes, as shown in FIG. 16, a connection member body 40 engaged with the guide member body 38 from a distal end side of the guide member body 38, and ten connection cylinders 41 projecting from the connection member body 40 radially outward centered on the rotation axis L1. The tube connection member 12 includes a plurality of connection cylinders in addition to the ten connection cylinders 41, but the connection cylinders other than the ten connection cylinders 41 are not shown in FIG. 16.

The connection member body 40 includes a communication passage 40a connecting with the air tube C2 introduced through the guide member body 38, and individual passages 40b extending from the communication passage 40a radially outward centered the rotation axis L1 and communicating with the connection cylinders 41.

The connection cylinders 41 are disposed at positions corresponding to the cooling jackets 17 in a direction along the circumference about the rotation axis L1.

Therefore, air introduced through the air tube C2 is distributed through the communication passage 40a, the individual passages 40b, and the connection cylinders 41 to be guided to the cooling jackets 17 through the air tubes C3 connected to the connection cylinders 41.

Each cooling jacket 17 includes two tube connection portions, one of which is used to supply air and the other of which is used to discharge air. The connection portion for air discharge is exposed to the air directly or via an unillustrated silencer.

As described, according to the invention specified in accordance with the above-described embodiment, the power transmission mechanism 7 distributes a power generated by the driving mechanism (the cam drum 3 and the cam follower 23) to the anvil 15 and the weight (the cam follower 23 and the holding member 24) in opposite directions. Therefore, it is possible to drive the holding member body 24a and the anvil 15 synchronously in the opposite directions.

Thus, an acceleration change of the anvil 15 can be offset by a reverse acceleration change of the hold member body 24a when the anvil 15 is driven. Therefore, it is possible to reduce vibration that occurs in the ultrasonic welding device 1.

Therefore, it is possible to reduce noise generated by movement of the anvil 15.

According to the above-described embodiment, the timing belt 30 is used to connect the cam follower 23 and the anvil holding mechanism 21. Therefore, the timing belt 30 can be used as a damper, owing to its flexibility, to absorb a shock generated when the anvil 15 is braked or activated. As a result, vibration caused by the shock can be reduced.

In the above-described embodiment, the timing belt 30 is described as an example of the endless belt. However, any belt in the form of a loop may be used as the endless belt. The endless belt includes not only those belts that are made originally in the form of a loop, but also those belts that are made to have a loop form by connecting the opposite end portions of open belts by adhesion, welding or joint members.

According to the above-described embodiment, the holding mechanism (the base 26, the brackets 27, the ceiling plate 31, the side plates 32 and the covering plate 33) holding the timing belt 30 and the timing pulleys 29 can be used to cover the long hole 5d, which makes it possible to prevent entry of foreign matter into the cam groove 3a.

The term "long hole" means a hole having a dimension in a moving direction (X direction) of the cam follower 23 longer than a dimension in a direction perpendicularly intersecting the moving direction. For example, the long hole may have a plane shape having a truck-like or substantially rectangular shape.

As described, in the case that the cam drum 3 is so configured that two anvils 15 provided at symmetric positions by 180 degrees around the rotation axis L1 synchronously move in opposite directions, it is possible, between the two anvils 15 provided at symmetric positions by 180 degrees around the rotation axis L1, to allow respective accelerations of the anvils 15 to offset each other and respective accelerations of the holding member bodies 24a to offset each other.

Therefore, in combination with the above-mentioned offset of the accelerations between the anvils 15 and the holding member bodies 24a, it is possible to reduce the vibration of the ultrasonic welding device 1 as a whole more effectively.

According to the invention specified in accordance with the above-described embodiment, the sheet W can be supported on a circumference centered on the rotation axis L1 by the plurality of sheet support members 44 disposed on the same circumference about the rotation axis L1.

Further, the attaching mechanism (the adjuster plate 5c and the attaching sections 18) allows the attaching positions of the plurality of sheet support members 44 to be adjusted in the radial directions centered on the rotation axis L1. Therefore, it is possible to easily change the length of the circumference over which the sheet support members 44 are disposed.

Therefore, it is possible to change the space between adjacent welding positions of the sheet W by the easy work of adjusting the attaching positions of the sheet support members 44.

According to the above-described embodiment, the sheet support members 44 are attached to the horn holding mechanisms 20, and the attaching sections 18 allow adjustment of the attaching positions of the horn holding mechanisms 20. As a result, the adjustment of the attaching positions of the horn holding mechanisms 20 also allows adjustment of the attaching positions of the sheet support members 44. This facilitates the adjustment of the space between adjacent welding positions.

Further, in the above-described embodiment, the horn holding mechanism 20 and the anvil holding mechanism 21 are connected via the base 19. Therefore, the attaching positions of the anvils 15, the horns 14, and the sheet support members 44 can be adjusted at once. This makes the adjustment of the space between adjacent welding positions extremely easy.

In the above-described embodiment, the surfaces of the support portions 44a of the sheet support members 44 are respectively disposed on both sides of each horn 14 in the direction along the circumference about the rotation axis L1. This allows the sheet W, even in the case that the space between adjacent welding positions is increased (in the case that adjacent horns 14 are spaced apart a greater distance), to be supported on both sides of and near each of the horns 14. As a result, the sheet W is welded in a stable position, which improves the welding accuracy.

In the above-described embodiment, the sheet support member 44 includes the support portion 44a and the bending portion 44b. As a result, a cavity is defined between each adjacent bending portions 44b of the sheet support members 44, the cavities recessed from the support portions 44a of the sheet support members 44. Therefore, thick portions (portions where the absorbers A are disposed: See FIG. 1) of the sheet W that each extend between adjacent welding target positions (weld sections S: See FIG. 1) can be placed in the cavities to thereby prevent the entire sheet W from rising from the sheet support members 44 due to the thick portions of the sheet W.

Therefore, it is possible to allow the sheet support members 44 to more reliably support the sheet W.

According to the invention exemplified by the above-described embodiment, the drive shaft 4 extends from a position on the base end side of the rotary support mechanical assembly (the disk 5a, the adjuster plate 5c, the attaching sections 18, and the sheet support members 44) to a position between the distal end E1 and the base end E2 of the rotary support mechanical assembly, unlike a conventional drive shaft provided at a position on the base end side of a drum. This makes it possible to rotatably support the rotary support mechanical assembly without the conventional stationary shaft provided for supporting the drum, by supporting an intermediate portion of the drive shaft 4 by the drive shaft support member 2.

Further, unlike the conventional stationary shaft, the distal end of the dive shaft 4 lies at a position on the base end side of a distal end surface of the rotary support member. This allows easy access to the rotary support mechanical assembly, the horns 14, and the anvils 15 from the distal end side of the rotary support mechanical assembly.

Further, a passage (the through hole 4b) defined in the drive shaft 4 is used as an arrangement route for the wires C1, the passage extending from the slip ring 8 disposed at the base end portion of the drive shaft 4 to the position between the distal end E1 and the base end E2 of the rotary support mechanical assembly as described. This allows at least a part of the wires C1 to be guided to the ultrasonic wave generators 16 through the inside of the rotary support mechanical assembly, unlike the conventional case where a wire is guided to a horn from the circumferential side of a drum.

Therefore, it is possible to prevent damage of a portion of the wires C1 between the slip ring 8 and the horns 14 while improving the maintainability of the horns and the anvils.

In the above-described embodiment, the slip ring 8 is described as an example of the rotary connector in which the electrical connection between the stationary terminals 34a and the rotary terminals 35a is maintained by the contact between the respective conductive contact parts. However, the rotary connector is not limited to the slip ring 8. For example, a rotary connector may be used in which conductive liquid metal is provided between a stationary terminal holding portion 34 and a rotary cylinder portion 35.

In the above-described embodiment, the ultrasonic wave generators 16 are disposed in the region on the rotation axis L1 side of the support portions 44a of the sheet support members 44 (inside the support portions 44a of the sheet support members 44). This allows the entire wires C1 to be placed in the region inside the rotary support mechanical assembly. Therefore, it is possible to prevent damage of the wires C1 more effectively.

In the above-described embodiment, the sheet W can be held, not on a drum as in the conventional cases, but on the plurality of sheet support members 44 disposed over the same circumference centered on the rotation axis 11. Therefore, the space inside the sheet support members 44 can be used as a space for arranging the wires C1.

According to the above-described embodiment, the wire guide member 11 is provided to make it possible to guide the wires C1 drawn out from the distal end of the drive shaft 4 to the destinations of the wires C1. Thus, the plurality of wires C1 can be guided to the ultrasonic wave generators 16 in a neat way.

Furthermore, because the wire guide member 11 is disposed at the position between the distal end E1 and the base end E2 of the rotary support mechanical assembly (the disk 5a, the adjuster plate 5c, the attaching sections 18, and the sheet support members 44), it is possible to arrange the plurality of wires C1 without affecting the maintainability of the rotary support mechanical assembly, the horns 14, and the anvils 15.

According to the above-described embodiment, the air tube C2 can be guided from the base end portion to the distal end portion of the drive shaft 4 through the inside of the drive shaft 4 with the wires C1, the air tube C2 constituting a part of the air circuit connecting the cooling jackets 17 and the rotary joint 9.

Therefore, it is possible to prevent damage of the air tube C2, as compared to the case of arranging the air tube C2 through the outside of the rotary support mechanical assembly.

The above-described embodiment illustrates a case where the horn 14 is secured to the rotary drum 5 and the anvil 15 is movable relative to the horn 14. However, it may be configured such that the anvil 15 is secured to the rotary drum 5 and the horn 14 is movable relative to the anvil 15.

The above-described embodiment illustrates a case where the timing belt 30 and the timing pulleys 29 are used as a structure for connecting the cam follower 23 and the anvil holding mechanism 21. However, the cam follower 23 and the anvil holding mechanism 21 may be connected via a link.

The above-described embodiment illustrates a case where the sheet support members 44 are attached to the horn holding mechanisms 20. However, the sheet support members 44 may be attached directly to the rotary drum 5. In this case, it is preferred to provide an attaching mechanism between the rotary drum 5 and the sheet support members 44, the attaching mechanism allowing the sheet support members 44 to be attached to the same circumference centered on the rotation axis L1 and allowing attaching positions of the sheet support members 44 to the rotary drum 5 to be adjusted in radial directions centered on the rotation axis L1.

The above-described embodiment illustrates a case where the surfaces of the support portions 44a (hereinafter, referred to as "support surfaces") are respectively disposed on both sides of each horn 14 in the direction along the circumference about the rotation axis L1. However, a support surface may be disposed only on one side of each horn 14 in the circumferential direction.

The above-described embodiment illustrates a case where a sheet support member 44 is disposed on each of both sides of the horn 14 in the circumferential direction. However, one sheet support member formed with a hole for exposing the horn 14 may be disposed to provide support surfaces on both sides of the horn 14 in the circumferential direction.

The above-described embodiment illustrates a case where the ultrasonic wave generators 16 are disposed in the region on the rotation axis L1 side of the support portions 44a of the sheet support members 44 (inside the support portions 44a of the sheet support members 44). However, the ultrasonic wave generators 16 may be disposed outside the support portions 44a. For example, in the case that the ultrasonic wave generators 16 are disposed at the positions where the anvils 15 are disposed in the above-described embodiment, it is possible to connect a wire C4 drawn out from the wire guide member 11 to an ultrasonic wave generator 16 by passing the wire C4 though the space between adjacent welding units 6, as shown by the dashed line in FIG. 13.

The above-described embodiment illustrates a case where the cam follower 23 and the holding member 24 function as a weight. However, the weight may be provided independently of the holding member 24. Alternatively, it may be configured such that only the cam follower 23 functions as a weight.

The above-described specific embodiment mainly includes the invention having the following configurations.

The present invention provides an ultrasonic welding device for ultrasonically welding an object to be welded, comprising: a rotary support mechanical assembly rotatable about a predetermined rotation axis and operable to support the object over a circumference centered on the rotation axis, the object being continuously supplied; and at least a pair of a horn and an anvil attached to the rotary support mechanical assembly to thereby revolve about the rotation axis and sandwich the object supported over the rotary support mechanical assembly to weld the object, when one of the horn and the anvil is defined as a first welding tool and the other of the horn and the anvil is defined as a second welding tool, the first welding tool being attached to the rotary support mechanical assembly in such a manner as to be movable relative to the second welding tool between a position to sandwich the object in cooperation with the second welding tool and a position away from the second welding tool, wherein the rotary support mechanical assembly includes a rotary member rotatable about the rotation axis, a plurality of object support members each having a support surface for supporting the object, and an attaching mechanism for allowing the plurality of object support members to be attached to the rotary member in a state that the object support members lie on the same circumference about the rotation axis, and allowing attaching positions of the object support members to the rotary member to be adjusted in radial directions centered on the rotation axis.

According to the present invention, it is possible to allow the plurality of object support members disposed on the same circumference about the rotation axis to support the object to be welded over the circumference centered on the rotation axis.

Further, the attaching mechanism allows the attaching positions of the plurality of object support members to be adjusted in the radial directions centered on the rotation axis. Therefore, it is possible to easily change the length of the circumference over which the object support members are disposed.

Therefore, according to the present invention, it is possible to change the space between adjacent welding positions of the object by the easy work of adjusting the attaching positions of the object support members.

In the present invention, the term "welding an object to be welded" includes welding of a plurality of objects to be welded that face each other, and welding of portions of an object to be welded that face each other as a result of folding up the object.

In the present invention, the term "to be adjusted in radial directions" includes not only the case where adjustment can be made in directions parallel to radials through the rotation axis, but also the case where adjustment can be made in a direction along the circumference about the rotation axis in addition to the directions parallel to radials through the rotation axis.

Thus, the term "to be adjusted in radial directions" means that the attaching positions of the object support members to the rotary member can be adjusted at least in the directions parallel to radials through the rotation axis.

Here, the plurality of object support members may be attached to the rotary support mechanical assembly, independently of the first welding tool and the second welding tool. However, in this case, it is necessary to adjust not only the attaching positions of the object support members, but also attaching positions of the first welding tool and the second welding tool.

Accordingly, in the above-described ultrasonic welding device, it is preferred that a plurality of pairs of first and second welding tools are included, that the rotary support mechanical assembly includes a plurality of second welding tool holding mechanisms for respectively holding the plurality of second welding tools, that the object support members are attached to the second welding tool holding mechanisms, and that the attaching mechanism allows the second welding tool holding mechanisms to be attached to the rotary member in a state that the second welding tool holding mechanisms lie on the same circumference about the rotation axis, and allows attaching positions of the second welding tool holding mechanisms to the rotary member to be adjusted in radial directions.

According to this configuration, the adjustment of the attaching positions of the second welding tool holding mechanisms also allows the adjustment of the attaching positions of the object support members. This therefore facilitates the adjustment of the space between adjacent welding positions.

Further, in the above-described ultrasonic welding device, the rotary support mechanical assembly is preferred to further include a plurality of first welding tool holding mechanisms respectively attached to the second welding tool holding mechanisms for holding the plurality of first welding tools in such a manner that the first welding tools are movable relative to the second welding tools.

According to this configuration, the attaching positions of the first welding tools, the second welding tools, and the object support members can be adjusted at once. This makes the adjustment of the space between adjacent welding positions extremely easy.

Here, an object support member may be disposed only on one side of each second welding tool in a direction along the circumference about the rotation axis. In this case, however, a portion of the object lying on the other side of the second welding tool is supported by an object support member disposed on an adjacent second welding tool holding mechanism. However, in the case that the space between adjacent welding positions is increased, adjacent two second welding tool holding mechanisms are disposed at a distance from each other. Therefore, in this case, it is difficult to reliably support the object.

Accordingly, it is preferred that the object support members are attached to the second welding tool holding mechanisms in such a manner that the support surfaces of the object support members respectively lie on both sides of each second welding tool in the direction along the circumference about the rotation axis.

According to this configuration, even in the case that the space between adjacent welding positions is increased, the object can be supported on both sides of and near each of the second welding tools. As a result, the object is welded in a stable position, which improves the welding accuracy.

In the above-described ultrasonic welding device, it is preferred that each of the plurality of object support members is preferred to include a support portion extending from the second welding tool in the circumferential direction and having the support surface, and a bending portion extending at an angle from a distal end of the support portion, the bending portion lying between a straight line connecting distal end portions of adjacent support portions of two second welding tools and the rotation axis.

According to this configuration, a cavity can be defined between each adjacent bending portions of the object support members, the cavities recessed form the support portions of the object support members. Therefore, in the case that the object includes thick portions that each extend between adjacent welding target positions set at intervals and that are thicker than the welding target positions, the thick portions of the object each extending between adjacent welding target positions can be placed in the cavities to thereby prevent the entire object from rising from the object support members due to the thick portions of the object.

Therefore, it is possible to allow the object support members to more reliably support the object.

The invention claimed is:

1. An ultrasonic welding device for ultrasonically welding an object to be welded, comprising:
a rotary support mechanical assembly rotatable about a predetermined rotation axis and operable to support the object over a circumference centered on the rotation axis, the object being continuously supplied; and
at least a pair of a horn and an anvil attached to the rotary support mechanical assembly to thereby revolve about the rotation axis and sandwich the object supported over the rotary support mechanical assembly to weld the object, when one of the horn and the anvil is defined as a first welding tool and the other of the horn and the anvil is defined as a second welding tool, the first welding tool being attached to the rotary support mechanical assembly in such a manner as to be movable relative to the second welding tool between a position to sandwich the object in cooperation with the second welding tool and a position away from the second welding tool, wherein
the rotary support mechanical assembly includes
a rotary member rotatable about the rotation axis,
a plurality of object support members each having a support surface for supporting the object,
an attaching mechanism for allowing the plurality of object support members to be attached to the rotary member in a state that the object support members lie on the same circumference about the rotation axis, and allowing attaching positions of the object support members to the rotary member to be adjusted in radial directions centered on the rotation axis, the attaching mechanism includes an attaching section attached to the rotary member to be adjusted in the radial directions centered on the rotation axis,
a first welding tool holding mechanism attached to the attaching section and holding the first welding tool, and
a second welding tool holding mechanism attached to the attaching section and holding the second welding tool, and the plurality of object support members are attached to the second welding tool.

2. An ultrasonic welding device according to claim 1, wherein
the ultrasonic welding device includes a plurality of pairs of first and second welding tools;
the rotary support mechanical assembly includes a plurality of second welding tool holding mechanisms for respectively holding the plurality of second welding tools;
and
the attaching mechanism allows the second welding tool holding mechanisms to be attached to the rotary member in a state that the second welding tool holding mechanisms lie on the same circumference about the rotation axis, and allows attaching positions of the second welding tool holding mechanisms to the rotary member to be adjusted in the radial directions.

3. An ultrasonic welding device according to claim 2, wherein
the rotary support mechanical assembly further includes a plurality of first welding tool holding mechanisms respectively attached to the second welding tool holding mechanisms for holding the plurality of first welding tools in such a manner that the first welding tools are movable relative to the second welding tools.

4. An ultrasonic welding device according to claim 2, wherein
the object support members are attached to the second welding tool holding mechanisms in such a manner that the support surfaces of the object support members respectively lie on both sides of each second welding tool in a direction along the circumference about the rotation axis.

5. An ultrasonic welding device according to claim 4, wherein
each of the plurality of object support members includes a support portion extending from the second welding tool in the circumferential direction and having the support surface, and a bending portion extending at an angle from a distal end of the support portion, the bending portion lying between a straight line connecting distal end portions of adjacent support portions of two second welding tools and the rotation axis.

* * * * *